US009810623B2

(12) United States Patent
Ghaffari et al.

(10) Patent No.: US 9,810,623 B2
(45) Date of Patent: Nov. 7, 2017

(54) QUANTIFICATION OF A CHANGE IN ASSAY

(71) Applicant: MC10, Inc., Cambridge, MA (US)

(72) Inventors: Roozbeh Ghaffari, Cambridge, MA (US); Alexander Aranyosi, Medford, MA (US); Stephen Lee, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 157 days.

(21) Appl. No.: 14/656,046

(22) Filed: Mar. 12, 2015

(65) Prior Publication Data

US 2015/0260713 A1    Sep. 17, 2015

Related U.S. Application Data

(60) Provisional application No. 61/952,076, filed on Mar. 12, 2014, provisional application No. 61/952,082, filed on Mar. 12, 2014.

(51) Int. Cl.
*B01L 3/00* (2006.01)
*G01N 21/00* (2006.01)
(Continued)

(52) U.S. Cl.
CPC .......... *G01N 21/272* (2013.01); *B01L 3/5055* (2013.01); *B01L 3/502715* (2013.01);
(Continued)

(58) Field of Classification Search
CPC ......... G01N 35/00871; G01N 35/0092; G01N 35/00029; G01N 2035/00138;
(Continued)

(56) References Cited

U.S. PATENT DOCUMENTS 3,716,861 A    2/1973   Root
3,805,427 A    4/1974   Epstein
(Continued)

FOREIGN PATENT DOCUMENTS

WO    WO 2005/122285 A2    12/2005
WO    WO 2008/030960 A2    3/2008
(Continued)

OTHER PUBLICATIONS

Omenetto et al., "A New Route for Silk," Nature Photonics, vol. 2, 641-643 (3 pages) (Nov. 2008).
(Continued)

*Primary Examiner* — Erik B Crawford
(74) *Attorney, Agent, or Firm* — Nixon Peabody LLP; David F. Crosby

(57) ABSTRACT

The present invention relates to portable devices for point-of-care diagnostics that can perform measurements on a sample (e.g., blood, serum, saliva, or urine) and relay data to an external device for, e.g., data analysis. The device can comprise a paper-based diagnostic substrate and a base substrate that include electronic circuitry and electronic elements necessary for performing the measurements. The device can also comprise an antenna for near field communication with an external device. Another aspect of the invention relates to methods of using these devices.

18 Claims, 12 Drawing Sheets

(51) Int. Cl.
  *G01N 21/01* (2006.01)
  *G01N 21/27* (2006.01)
  G01N 35/00 (2006.01)
  G01N 21/77 (2006.01)

(52) U.S. Cl.
  CPC ... *B01L 2200/025* (2013.01); *B01L 2300/023* (2013.01); *B01L 2300/0636* (2013.01); *B01L 2300/0816* (2013.01); *B01L 2300/0864* (2013.01); *G01N 35/00871* (2013.01); *G01N 2021/7783* (2013.01); *G01N 2035/00881* (2013.01)

(58) Field of Classification Search
  CPC .......... G01N 2035/00148; G01N 2035/00237; G01N 33/54306; G01N 33/54313; G01N 33/54366; G01N 15/14; G01N 2021/6419; G01N 2201/06113; G01N 33/5302; G01N 35/00; G01N 15/0205; G01N 2021/6439; G01N 33/54346; G01N 21/272; G01N 2021/77; B01L 9/527; B01L 2300/0816; B01L 2200/027; B01L 2300/0627; B01L 2300/0636; B01L 2300/087; B01L 3/502761; B01L 2300/023; B01L 2300/043; B01L 2400/0406; B01L 3/5055; A61B 2562/164; A61B 5/0059; A61B 5/6833; A61B 2562/046; A61B 5/145; A61B 2562/0233; A61B 2562/166; A61B 5/6867; A61B 2560/0412; A61B 5/02438; A61B 5/681; A61B 5/6824; A61B 5/6832; A61B 8/4236; A61B 21/272
  See application file for complete search history.

(56) References Cited

U.S. PATENT DOCUMENTS

| | | | |
|---|---|---|---|
| 5,817,008 | A | 10/1998 | Rafert et al. |
| 5,907,477 | A | 5/1999 | Tuttle et al. |
| 6,063,046 | A | 5/2000 | Allum |
| 6,784,844 | B1 | 8/2004 | Boakes et al. |
| 7,265,298 | B2 | 9/2007 | Maghribi |
| 7,302,751 | B2 | 12/2007 | Hamburgen |
| 7,337,012 | B2 | 2/2008 | Maghribi |
| 7,487,587 | B2 | 2/2009 | Vanfleteren |
| 7,491,892 | B2 | 2/2009 | Wagner |
| 7,521,292 | B2 | 4/2009 | Rogers |
| 7,557,367 | B2 | 7/2009 | Rodgers |
| 7,618,260 | B2 | 11/2009 | Daniel et al. |
| 7,622,367 | B1 | 11/2009 | Nuzzo |
| 7,759,167 | B2 | 7/2010 | Vanfleteren |
| 7,960,246 | B2 | 6/2011 | Flamand |
| 7,982,296 | B2 | 7/2011 | Nuzzo |
| 8,097,926 | B2 | 1/2012 | De Graff |
| 8,198,621 | B2 | 6/2012 | Rogers |
| 8,207,473 | B2 | 6/2012 | Axisa |
| 8,217,381 | B2 | 7/2012 | Rodgers |
| 8,372,726 | B2 | 2/2013 | De Graff |
| 8,389,862 | B2 | 3/2013 | Arora |
| 8,431,828 | B2 | 4/2013 | Vanfleteren |
| 8,440,546 | B2 | 5/2013 | Nuzzo |
| 8,536,667 | B2 | 9/2013 | De Graff |
| 8,552,299 | B2 | 10/2013 | Rodgers |
| 8,664,699 | B2 | 3/2014 | Nuzzo |
| 8,679,888 | B2 | 3/2014 | Rodgers |
| 8,729,524 | B2 | 5/2014 | Rodgers |
| 8,754,396 | B2 | 6/2014 | Rogers |
| 8,865,489 | B2 | 10/2014 | Rodgers |
| 8,886,334 | B2 | 11/2014 | Ghaffari |
| 8,905,772 | B2 | 12/2014 | Rodgers |
| 9,012,784 | B2 | 4/2015 | Arora |
| 2002/0094701 | A1 | 7/2002 | Biegelsen et al. |
| 2002/0113739 | A1 | 8/2002 | Howard |
| 2003/0214408 | A1 | 11/2003 | Grajales |
| 2004/0243204 | A1 | 12/2004 | Maghribi |
| 2005/0096513 | A1 | 5/2005 | Ozguz |
| 2006/0038182 | A1 | 2/2006 | Rodgers |
| 2006/0264767 | A1 | 11/2006 | Shennib |
| 2006/0286785 | A1 | 12/2006 | Rogers |
| 2007/0123756 | A1 | 5/2007 | Kitajima et al. |
| 2008/0046080 | A1 | 2/2008 | Vanden Bulcke |
| 2008/0139894 | A1 | 6/2008 | Szydlo-Moore et al. |
| 2008/0157235 | A1 | 7/2008 | Rodgers |
| 2008/0204021 | A1 | 8/2008 | Leussler et al. |
| 2008/0249576 | A1 | 10/2008 | Johnson et al. |
| 2009/0000377 | A1 | 1/2009 | Shipps et al. |
| 2009/0048556 | A1 | 2/2009 | Durand |
| 2009/0107704 | A1 | 4/2009 | Vanfleteren |
| 2009/0261828 | A1 | 10/2009 | Nordmeyer-Massner |
| 2009/0294803 | A1 | 12/2009 | Nuzzo |
| 2009/0322480 | A1 | 12/2009 | Benedict et al. |
| 2010/0002402 | A1 | 1/2010 | Rogers |
| 2010/0059863 | A1 | 3/2010 | Rogers |
| 2010/0072577 | A1 | 3/2010 | Nuzzo |
| 2010/0087782 | A1 | 4/2010 | Ghaffari |
| 2010/0090824 | A1 | 4/2010 | Rowell et al. |
| 2010/0116526 | A1 | 5/2010 | Arora |
| 2010/0178722 | A1 | 7/2010 | De Graff |
| 2010/0245011 | A1 | 9/2010 | Chatzopoulos et al. |
| 2010/0271191 | A1 | 10/2010 | De Graff |
| 2010/0298895 | A1 | 11/2010 | Ghaffari |
| 2010/0317132 | A1 | 12/2010 | Rodgers |
| 2010/0321161 | A1 | 12/2010 | Isabell |
| 2011/0034912 | A1 | 2/2011 | De Graff |
| 2011/0054583 | A1 | 3/2011 | Litt |
| 2011/0101789 | A1 | 5/2011 | Salter et al. |
| 2011/0121822 | A1 | 5/2011 | Parsche |
| 2011/0140897 | A1 | 6/2011 | Purks et al. |
| 2011/0184320 | A1 | 7/2011 | Shipps |
| 2011/0215931 | A1 | 9/2011 | Callsen |
| 2011/0218756 | A1 | 9/2011 | Callsen |
| 2011/0218757 | A1 | 9/2011 | Callsen |
| 2011/0220890 | A1 | 9/2011 | Nuzzo |
| 2011/0235041 | A1* | 9/2011 | Rao ............... G08B 21/12 356/437 |
| 2011/0277813 | A1 | 11/2011 | Rodgers |
| 2012/0016258 | A1 | 1/2012 | Webster et al. |
| 2012/0051005 | A1 | 3/2012 | Vanfleteren |
| 2012/0052268 | A1 | 3/2012 | Axisa |
| 2012/0065937 | A1 | 3/2012 | De Graff |
| 2012/0087216 | A1 | 4/2012 | Keung et al. |
| 2012/0092178 | A1 | 4/2012 | Callsen |
| 2012/0092222 | A1 | 4/2012 | Kato et al. |
| 2012/0157804 | A1 | 6/2012 | Rodgers |
| 2012/0172697 | A1 | 7/2012 | Urman |
| 2012/0226130 | A1 | 9/2012 | De Graff |
| 2012/0244848 | A1 | 9/2012 | Ghaffari |
| 2012/0256308 | A1 | 10/2012 | Helin |
| 2012/0316455 | A1 | 12/2012 | Rahman et al. |
| 2012/0327608 | A1 | 12/2012 | Rodgers |
| 2013/0041235 | A1 | 2/2013 | Rogers et al. |
| 2013/0099358 | A1 | 4/2013 | Elolampi |
| 2013/0100618 | A1 | 4/2013 | Rogers |
| 2013/0118255 | A1 | 5/2013 | Callsen |
| 2013/0150693 | A1 | 6/2013 | D'angelo |
| 2013/0185003 | A1 | 7/2013 | Carbeck |
| 2013/0192356 | A1 | 8/2013 | De Graff |
| 2013/0200268 | A1 | 8/2013 | Rafferty |
| 2013/0211761 | A1 | 8/2013 | Brandsma et al. |
| 2013/0225965 | A1 | 8/2013 | Ghaffari |
| 2013/0245388 | A1 | 9/2013 | Rafferty |
| 2013/0274562 | A1 | 10/2013 | Ghaffari |
| 2013/0313713 | A1 | 11/2013 | Arora |
| 2013/0316487 | A1 | 11/2013 | De Graff |
| 2013/0320503 | A1 | 12/2013 | Nuzzo |
| 2014/0001058 | A1 | 1/2014 | Ghaffari |
| 2014/0012160 | A1 | 1/2014 | Ghaffari |
| 2014/0012242 | A1 | 1/2014 | Lee |
| 2014/0022746 | A1 | 1/2014 | Hsu |
| 2014/0039290 | A1 | 2/2014 | De Graff |
| 2014/0097944 | A1 | 4/2014 | Fastert |

(56) References Cited

U.S. PATENT DOCUMENTS

| | | |
|---|---|---|
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora et al. |
| 2015/0099976 A1 | 4/2015 | Ghaffari et al. |
| 2015/0100135 A1 | 4/2015 | Ives |
| 2015/0107993 A1* | 4/2015 | Izquierdo ............ C12Q 1/02 204/403.01 |

FOREIGN PATENT DOCUMENTS

| | | |
|---|---|---|
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/049716 A1 | 4/2013 |
| WO | WO 2013/052919 A2 | 4/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |

OTHER PUBLICATIONS

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

* cited by examiner

QUANTIFICATION OF A CHANGE IN ASSAY

CROSS-REFERENCE TO RELATED APPLICATION

This application claims benefit under 35 U.S.C. §119(e) of U.S. Provisional Application No. 61/952,076 filed Mar. 12, 2014 and 61/952,082 filed Mar. 12, 2014, the contents of each of which are incorporated herein by reference in their entirety.

TECHNICAL FIELD

The present invention relates generally to point-of-care diagnostics and paper-based diagnostic devices.

BACKGROUND

Micronutrient deficiency is a common health risk in developing countries, affecting a sizable portion of the world's population. For example, iron deficiency anemia impairs mental development, decreases energy, and can cause death in childbirth. Micronutrient deficiency can be assessed by measuring the levels of proteins such as ferritin, retinol binding protein (RBP), C-reactive protein (CRP), and alpha-1-acid glycoprotein (AGP), depending on the type of the deficiency.

Diagnosis of micronutrient deficiency is especially needed in remote areas with limited access to power and other resources. Low-cost portable tests tend to have low resolution, impeding measurement accuracy. High quality quantitative tests require samples to be collected and sent to a facility with the appropriate instruments. A wait time of about one month is common.

Microfluidic measurement devices have gained popularity as low-cost, point-of-care, and rapid diagnostic tools (Hu et al., Biosensors and Bioelectronics 2014, 54, 585-597; Martinez et al., Angew. Chem. Int. Ed. 2007, 46, 1318-1320). Scientists are developing microfluidic measurement devices for a wide range of functions, from rapid point-of-care measurement of liver enzyme levels to routine evaluation of heavy metal contamination in reservoir water (Pollock et al., PLoS ONE 2013, 8, e75616; Wang et al. 2014, Anal Bioanal Chem 406, 2799-2807). Many microfluidic measurement devices use either chemical reactions or antigen-antibody binding to produce a color change that correlates with the target analyte concentration (Hu et al., Biosensors and Bioelectronics 2014, 54, 585-597). Unlike their lateral flow assay (LFA) predecessors, these devices are often highly multiplexed with complex geometries and multi-color readouts. Moreover, color change may depend on time, temperature and humidity (Pollock et al., PLoS ONE 2013, 8, e75616). Together, these complexities make it difficult for a user to visually interpret the color change and accurately assign concentration values.

The increasing complexity of microfluidic measurement devices necessitates the development of novel methods for data acquisition and management to maintain assay objectivity and obtain quantitative measurements. Though several methods exist to read colorimetric assays, various constraints limit their utility. Line scan readers, such as the ESEQuant Lateral Flow System (Qiagen, CA, USA), successfully collect data from LFAs. However, they are incompatible with the complex geometries often found in microfluidic measurement devices. Charge-coupled device (CCD)-based readers capture data quickly over a wide area, but are often expensive and require skilled image analysis (Gui et al., Nanoscale Res Lett 2014, 9, 1-8). Smart phone cameras and corresponding applications capture assay images and compare assay color development to an accompanying color chart (Wang et al. 2014, Anal Bioanal Chem 406, 2799-2807). While these offer a simple, cost-effective solution for point-of-care assays, results are vulnerable to changes in environmental lighting, photo angle and depth, and differences in the make/model of the phone. Similarly, cell phone-attached, enclosed LFA readers, which attach to the back of a cell phone and use internal LEDs for illumination, continue to use a cell phone's camera making them dependent on the make/model of the phone (Mudanyali et al., Lab Chip 2012, 12, 2678). Lastly, as some of these microfluidic measurement devices are based on paper, portable light reflectance readers, which collect data on signal intensity by measuring the light reflected from the surface of an assay, lack sensitivity because they are not able to sample the density of absorbers throughout the thickness of the paper (Lee et al., Lab Chip 2010, 11, 120; Li et al., ELECTROPHORESIS 2014, 35, 1152-1159; Yamaguchi et al., Bioelectronics 2005, 21, 426-432).

In view of the above, there is an unmet need in the art for novel devices and/or methods for extracting quantitative information from microfluidic measurement devices.

SUMMARY

The technology described herein relates to measurement devices that have built-in components for performing the measurements. Data can be transmitted to an external device for analysis and displaying a quantitative result, e.g., the level of a target protein in a blood sample.

In one aspect, the technology described herein relates to a measurement device comprising (1) a diagnostic substrate comprising (a) a sample receiver to receive a sample, wherein the sample receiver is at least partially formed in or disposed on the diagnostic substrate; (b) a fluidic channel connected to the sample receiver; (c) a detection region at least partially formed in or disposed on the diagnostic substrate, wherein the detection region is coupled to the sample receiver by the fluidic channel; (d) a control region at least partially formed in or disposed on the diagnostic substrate, wherein the control region is coupled to the detection region by the fluidic channel, and (2) a base substrate comprising (e) an antenna for near-field communication (NFC) at least partially formed in or disposed on the base substrate; (f) electronic circuitry connected to the antenna and at least partially formed in or disposed on the base substrate, wherein the electronic circuitry generates data as a function of an output signal from the sample or a derivative thereof; (g) a first portion comprising a first photodetector and a second photodetector connected to the electronic circuitry and at least partially formed in or disposed on the first portion; (h) a second portion comprising a first light source and a second light source connected to the electronic circuitry and at least partially formed in or disposed on the second portion, wherein the first portion and the second portion are positioned to align the photodetectors and the light sources such that light from the first light source passes through the detection region and gets detected by the first photodetector, the light from the second light source passes through the control region and gets detected by the second photodetector, and (i) a thin-film battery connected to the electronic circuitry and configured to provide power to the at least one photodetector and light source.

In accordance with some embodiments of the invention, the diagnostic substrate further comprises a reagent to react with the sample or the derivative of the sample.

In accordance with some embodiments of the invention, the reagent is a plurality of dyed nanoparticles.

In accordance with some embodiments of the invention, the measurement device further comprises a data storage device connected to the electronic circuitry and configured to store the data.

In accordance with some embodiments of the invention, the measurement device further comprises a sensor coupled to the sample receiver to detect the presence of the sample. In accordance with some embodiments of the invention, the sensor is polled periodically or according to a pre-set schedule to determine the presence of the sample. In accordance with some embodiments of the invention, the sensor is deactivated after the predetermined time.

In accordance with some embodiments of the invention, the measurement device further comprises a timer coupled to the sensor and the photodetector, wherein the timer is activated for a predetermined time when the sample is detected, the predetermined time representing the amount of time to read the sample, the timer activating the photodetector after the predetermined time has been reached, the photodetector outputting a measurement value.

In accordance with some embodiments of the invention, the measurement device further comprises a housing for enclosing at least a portion of the measurement device.

In accordance with some embodiments of the invention, the measurement device is initiated or activated by an external device through a first NFC transaction.

In accordance with some embodiments of the invention, the measurement device transmits the data to the external device through a second NFC transaction, whereby the external device processes the data to provide quantitative information related to the sample.

In accordance with some embodiments of the invention, the external device is a hand-held device or a wearable device.

In accordance with some embodiments of the invention, the quantitative information comprises at least one of: a glucose level; a T-cell concentration; a microorganism concentration; a water-based pathogen concentration; a bovine serum albumin (BVA) concentration; a bacterial concentration; a viral load; an antigen level; an antibody level; a diagnosis of tuberculosis; a diagnosis of dengue fever; a cardiac enzyme concentration; and a diagnosis of malaria.

In accordance with some embodiments of the invention, the first portion is folded over the second portion such that the first portion and the second portion sandwich the diagnostic substrate.

In accordance with some embodiments of the invention, the second portion is folded over the first portion such that the first portion and the second portion sandwich the diagnostic substrate.

In accordance with some embodiments of the invention, the sample is a fluid sample.

In accordance with some embodiments of the invention, the fluid sample is selected from the group consisting of blood, serum, saliva, and urine.

In accordance with some embodiments of the invention, the diagnostic substrate comprises a paper-based portion.

In another aspect, the technology described herein relates to a measurement device for measuring a value from a sample, the device comprising (1) a sample receiver for receiving a sample; (2) a sensor coupled to the sample receiver to detect the presence of the sample; (3) a detection region fluidly coupled to the sample receiver via a fluidic channel, thereby receiving the sample or a derivative thereof from the sample receiver; (4) a detector coupled to the detection region and configured to read a characteristic of the sample or the derivative thereof; and (5) a timer coupled to the sensor and the detector, wherein the timer is activated for a predetermined time when a sample is detected, the predetermined time representing the amount of time to read the sample, the timer activating the detector after the predetermined time has been reached, the detector outputting a measurement value.

In accordance with some embodiments of the invention, the sample is a fluid sample.

In accordance with some embodiments of the invention, the sensor comprises a light source and a photodetector, wherein the light source and the photodetector are positioned such that light from the light source passes through the sample receiver and gets detected by the photodetector.

In accordance with some embodiments of the invention, a change in transmission detected by the sensor indicates the presence of the sample.

In accordance with some embodiments of the invention, the sensor comprises electrical components configured to detect an electrical signal from the sample.

In accordance with some embodiments of the invention, a change in electrical conductivity detected by the sensor indicates the presence of the sample.

In accordance with some embodiments of the invention, the sensor is polled periodically or according to a pre-set schedule to determine the presence of the sample.

In accordance with some embodiments of the invention, the sensor is deactivated after the predetermined time.

In accordance with some embodiments of the invention, the measurement device further comprises a communications interface coupled to the sample receiver, the communications interface receiving a command signal from an external device to initiate the accepting of the sample. In accordance with some embodiments of the invention, the communications interface sends a signal indicative of the measured value.

In accordance with some embodiments of the invention, the external device is a hand-held device or a wearable device.

In accordance with some embodiments of the invention, the measurement device further comprises a data storage device coupled to the detector, the detector storing the measured value in the data storage device.

In accordance with some embodiments of the invention, the fluid sample is selected from the group consisting of blood, serum, saliva, and urine.

In yet another aspect, the technology described herein relates to a method of providing quantitative information on a sample using a measurement device disclosed herein, the method comprising (i) initiating the measurement device with an external device through a first near-field communication (NFC) transaction, wherein the measurement device performs a first transmission measurement on the detection region and the control region to produce a first data; (ii) contacting the sample receiver of the measurement device with the sample, wherein the measurement device performs a second transmission measurement on the detection region and the control region at a first predetermined time period after the contacting to produce a second data; (iii) performing a third transmission measurement on the detection region and the control region at a second predetermined time period after the second transmission measurement to produce a third data; (iv) transferring the first, second, and third data from the measurement device to the external device through a second NFC transaction; and (v) providing quantitative information based on analysis of the first, second, and third data.

In accordance with some embodiments of the invention, the sample is a fluid sample.

In accordance with some embodiments of the invention, the analysis comprises normalizing the third data against the first and second data.

In accordance with some embodiments of the invention, the method further comprises storing the first, second, and third data in a data storage device prior to the transferring.

In accordance with some embodiments of the invention, the external device is a hand-held device or a wearable device.

In accordance with some embodiments of the invention, the quantitative information comprises at least one of: a glucose level; a T-cell concentration; a microorganism concentration; a water-based pathogen concentration; a bovine serum albumin (BVA) concentration; a bacterial concentration; a viral load; an antigen level; an antibody level; a diagnosis of tuberculosis; a diagnosis of dengue fever; a cardiac enzyme concentration; and a diagnosis of malaria.

In accordance with some embodiments of the invention, the fluid sample is selected from the group consisting of blood, serum, saliva, and urine.

In accordance with some embodiments of the invention, the first and second light sources each gradually increases the light intensity during each of the transmission measurements, and the first and second photodetectors each detects light transmission in response to the increase in light intensity.

BRIEF DESCRIPTION OF THE DRAWINGS

(FIG. 4A) The assay consisted of a single paper layer enclosed by top and bottom laminate layers. (FIG. 4B) The wax-printed paper layer consisted of a sample port and four individual arms. Each arm had two circular areas, a storage zone where reagents were dried on the paper and a read zone, where color developed. After serum was applied to the sample port, capillary forces in the paper rapidly distributed the serum into the four individual arms of the assay filling up the storage zone and read zone consecutively. (FIG. 4C) Equations of chemical reactions (1-3) used to form a blue dye complex at a rate that corresponds with the ALT concentration in the applied serum. Alanine transaminase (ALT), pyruvate oxidase (PO), thiamine diphosphate (TPP), 4-aminoantipyrine (4-AAP) and N-ethyl-N-(2-hydroxy-3-sylfopropyl)-3,5-dimethoxy-alanine (DAOS).

(FIG. 5A) The reader consists of photodetectors that have been placed on a rigid metal board. Attached through a hinge, is a lid that contains the LEDs. The hinge allows for easy placement of the paper assay between the LEDs and PDs and provides repeatable alignment of the LEDs and PDs. Between the paper assay and electronics, two plastic spacers have been added to control the paper-area analyzed by the LEDs/PDs and to prevent the LEDs/PDs from pressing into the paper and damaging the fibrous structure. The entire system is connected through a USB port to a laptop where software collects and analyzes data from the system. (FIG. 5B) An LED/PD pair surrounds the read zone on each arm of the assay. When there are low ALT levels and little blue dye complex forms, most of the light from the red LEDs passes through the read zone and is detected by the PD. When there are high ALT levels and a lot of blue dye complex forms, most of the light from the red LEDs is absorbed or scattered by the read zone and little light is detected by the PD. (FIG. 5C) Diagram of internal electronics.

(FIG. 6A) Fluid volume lost from the device over a 15-minute period. (FIG. 6B) Change in light transmittance at read zones during over a 15-minute period. Values indicate the percentage of light transmission as calculated by the gain at the time of measurement versus the difference between the initial wet gain minus the dry state gain. Bars indicate standard errors.

(FIG. 8A) Gain values were normalized to the 300 second value for each read zone. All values at a given concentration were averaged. (FIG. 8B) Reaction velocities were calculated as the normalized gain versus time for each read zone between 300 and 600 seconds. Average and standard errors of the slope value at different ALT concentrations are plotted. n=≥4. *** indicates a p-value<0.001.

(FIG. 9A) Representative images of read zones for each ALT concentration. (FIG. 9B) The pixel intensity of the read zones was analyzed in image J. The average pixel intensities and standard errors are plotted for each ALT concentration. n=≥4. N.S. indicates non-significant.  indicates a p-value of <0.01 and * indicates a p-value<0.001. Different concentrations of blue dye are added to paper assays and measurements are read with Analyte Tester II and the scanner/Image J.

DETAILED DESCRIPTION

Figure 1A:
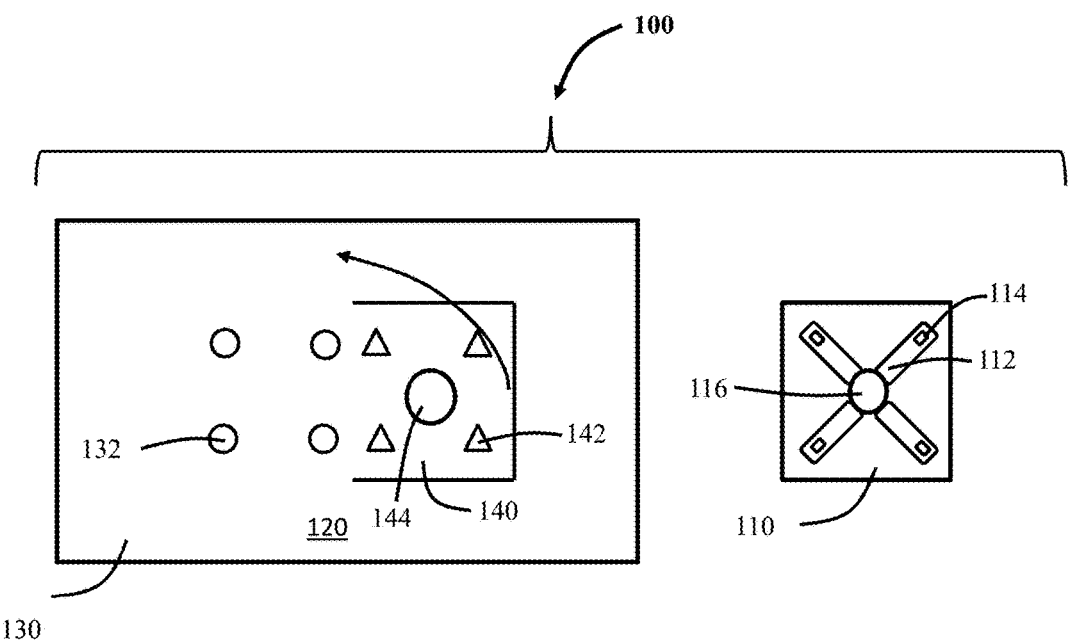
FIG. 1A illustrates a device 100 in accordance with some embodiments of the invention.

According to the example systems, methods, and apparatus described herein, one aspect of the technology described herein relates to quantifying a colorimetric change at a portion of the measurement device, such as but not limited to the detection region or other portion of the example measurement device. As a non-limiting example, the measured colorimetric change at the portion of the example measurement devices can be based on detection of an amount of a sample disposed on the sample receiver portion or an amount of a sample that reaches a measurement line or a control line of a fluid conduit (such as but not limited to a fluidic channel). The example measurement devices can be configured for detecting a colorimetric change due to the detection and/or quantification of at least one constituent of the sample, such as but not limited to a biological sample or other chemical sample.

Embodiments of the example systems, methods, and apparatus described herein exploit the physics of the effect of disposing a sample at a portion of the measurement device, such as but not limited to the sample receiver or other portion of the example measurement device (including the measurement line or control line). For example, dropping blood into a sample receiver portion of a microfluidic channel can cause a colorimetric change that is used to determine the start of monitoring the time it would take to get an accurate measurement result.

Any of the example methods according to the principles described herein may be implemented using a quantitative device that includes a receiver for receiving an amount of a sample, including blood or other type of biological, chemical or environmental sample.

The example systems, methods and apparatus can be configured to measure the change in optical transmissivity of a portion of the measurement device, such as but not limited to the sample receiver or other portion of the example measurement device, including any membrane portion of the sample conduit. In any example herein, the sample conduit can be a fluidic channel such as a microfluidic channel. The change in colorimetric properties can result from a biochemical assay at the portion of the measurement device that induces a color change or change in opacity.

In any example herein, the chemistry of the colorimetric change may differ depending on the chemistry of the reaction of the sample with the assay (e.g., the time of the reaction, the wavelength of color change due to the reaction, and/or change in optical response of the region where the reaction occurred). In any example herein, the chemistry of the colorimetric change may differ depending on the type of substrate or other membrane forming the region of interest of the measurement device, such as but not limited to any paper-based portion, glass-based portion, or any polymer-based portion. For example, the type of material can affect the chemistry of the reaction of the sample with the assay, or could block the amount of electromagnetic radiation transmitted to the detector. In another example, the types of electromagnetic radiation source and/or type of detectors used may influence the detection range of the system.

In an example implementation, a colorimetric change may be used for detecting the presence of the sample. When no blood or other sample is present at a portion of the measurement device, the color and/or opacity of the portion of measurement device is based on, e.g., the material of the substrate present at the portion of the device. The measurement device may include an electromagnetic radiation source, such as but not limited to an LED, to illuminate a portion of the measurement device. A detector, such as but not limited to a photodetector (e.g., an active-pixel sensor, a charge-coupled device, a photodiode, a photoresistor, a photovoltaic cell, a photomultiplier tube, or a phototransistor), can be used to measure the intensity, electromagnetic wavelength(s), or other quantifiable measure of the electromagnetic signal that passes through the portion of the measurement device and is detected by the detector. When an amount of blood or other sample reaches that portion of the measurement device, the color and/or opacity of that portion is configured to change. The electromagnetic radiation source, such as but not limited to a LED, is used to illuminate the portion of the measurement device. The detector, such as but not limited to a photodetector, can be used to measure any difference in the intensity, electromagnetic wavelength(s), or other quantifiable measure of the portion of the measurement device based on the presence of the blood or other sample. The example systems, methods and apparatus herein provide for improved signal at the detector with reduced noise.

An example system, method and apparatus herein facilitates detection of a change in light transmission resulting from the biochemical binding reaction. As non-limiting examples, the reaction can be a sandwich assay that becomes darker when higher amount of the constituent of interest in the sample is present, a competitive assay that becomes darker when smaller amount of the constituent of interest in the sample is present, or an enzymatic assay where the rate of color change over time varies with the concentration of a protein or enzyme of interest.

FIG. 1A is an illustration of a measurement device 100 in accordance with some embodiments of the invention. The device 100 can comprise a diagnostic substrate 110, a base substrate 120 comprising a first portion 130 and a second portion 140. The device 100 can be portable. In accordance with some embodiments of the invention, the measurement device 100 is for one-time use. In accordance with some embodiments of the invention, the diagnostic substrate 110 is for one-time use, and the base substrate 120 can be used multiple times (e.g., 2, 3, 4, 5, 6, 7, or more).

The diagnostic substrate 110 can comprise one or more (e.g., 2, 3, 4, 5, 6, 7, or more) fluidic channel 112 formed thereon, a detection region 114 formed within the fluidic channel 112, and a sample receiver 116 fluidicly coupled to the fluidic channel 112. In accordance with some embodiments of the invention, the diagnostic substrate 110 can comprise a paper-based portion, and the fluidic channel 112 and sample receiver 116 are at least partially formed in or disposed on the paper-based portion.

The base substrate 120 can comprise an antenna (not shown) for near-field communication (NFC) at least partially formed in or disposed on the base substrate 120. Antenna design for NFC is known in the art and is not discussed in detail here. The base substrate 120 can comprise electronic circuitry (not shown) connected to the antenna and at least partially formed in or disposed on the base substrate 120. The electronic circuitry can generate data as a function of an output signal from the sample or a derivative thereof. The base substrate 120 can comprise a power source (not shown, e.g., a thin-film battery) connected to the electronic circuitry. Alternative to the thin-film battery, other types of power sources can be included in the device 100. Such a power source may include, for example, a battery, a capacitor, a supercapacitor, a solar cell such as an organic photovoltaic cell, and/or an energy-harvesting device such as an inductive coupling coil, etc.

The first portion 130 can comprise one or more (e.g., 2, 3, 4, 5, 6, 7, or more) photodetector 132 at least partially formed in or disposed on the first portion 130. The photodetector 132 can be connected to the electronic circuitry. When there are two or more photodetectors, they can be arranged in any predetermined pattern including, but not limited to, random, circular, pentagonal, and hexagonal. The second portion 140 can comprise one or more (e.g., 2, 3, 4, 5, 6, 7, or more) light source 142 formed thereon. When there are two or more light sources, they can be arranged in any predetermined pattern including, but not limited to, random, circular, pentagonal, and hexagonal. The locations of the photodetector 132 and the light source 142 are positioned in such a manner that when the second portion 140 is folded over to sandwich the diagnostic substrate 110 between the first portion 130 and the second portion 140, the light produced by the light source 142 can pass through the detection region 114 and get detected by the photodetector 132. The second portion 140 can comprise a cutout 144 to allow the sample to contact with the sample receiver 116. In accordance with some embodiments of the invention, the first portion 130, the second portion 140, and a diagnostic substrate 110 can each comprise one or more alignment markers to facilitate the alignment process. In accordance with some embodiments of the invention, the alignment markers can be cutouts that permit precise alignment using external posts. These posts can be physically separate from the device, or can be incorporated into a mechanical spacer that separates portions 140 and 130 by a precise distance while holding substrate 110 between them. While FIG. 1A illustrates that the light source 142 is on the portion being folded over, it is contemplated that the photodetector 132 can be on the portion being folded over.

This folding mechanism permits the control of the distance between the photodetector 132 and the light source 142. After the folding, a thin-film battery (e.g., a paper-based battery) can be placed at the pre-folding position of the second portion 140 to connect to the electronic circuitry of the device 100.

In accordance with some embodiments of the invention, the second portion 140 is not physically linked to the first portion 130. In these embodiments, no folding is necessary.

The light source can be any solid-state emitting devices including but not limited to an organic or inorganic light-emitting diode, and a laser. In accordance with some embodiments of the invention, the device 100 can further include a first filter disposed between the sample and the photodetector to obtain a substantially monochromatic transmission light. In one example, the device 100 can further include a second filter disposed between the light source and the sample. The second filter is not needed if a monochromatic light source is used as the light source.

In some examples, a plurality of second filters is disposed between a broad-band light source and the sample to obtain a multi-channel spectrum of light to illuminate the sample. Spectral information from the sample can thus be obtained. Alternatively, a plurality of narrow-band light sources can be adopted without the use of the plurality of second filters.

Generally, the light source and photodetector may form a substantially matched pair of an optical generator and detector. The photodetector can be selected to be substantially sensitive to the color band/wavelength(s) of radiation generated by the light source. For example, a photodiode sensitive to the same color as the illumination LED may be used to detect the light from the illumination LED as much as possible.

Particular colors/wavelengths of interest for the light source and photodetector may be based, at least in part, on one or more of the nature of the sample to be measured/analyzed, the reagent employed, expected concentrations of analyte, and expected degree of reaction based on the particular reagent employed. Accordingly, in some example implementations of the concepts described herein, integrated devices for quantitative assays and diagnostics may include LED-photodector pairs and electronic circuitry to provide optical detection channels sensitive to particular colors/wavelength bands based on a particular type of sample for which the device is configured to provide quantitative information.

The power source can drive the electronic circuitry, light source and the photodetector with a variety of drive configurations, such as a constant current source, pulse-width modulation (PWM) for control and energy savings, or a buck-boost power configuration.

In accordance with some embodiments of the invention, the device 100 can further comprise a data storage device connected to the electronic circuitry and configured to store the data. The data storage device can include volatile and nonvolatile, removable and non-removable tangible media implemented in any method or technology for storage of information such as computer readable instructions, data structures, program modules or other data. Examples of applicable data storage device include, but are not limited to, RAM (random access memory), ROM (read only memory), EPROM (erasable programmable read only memory), EEPROM (electrically erasable programmable read only memory), and flash memory or other memory technology.

Figure 1B:
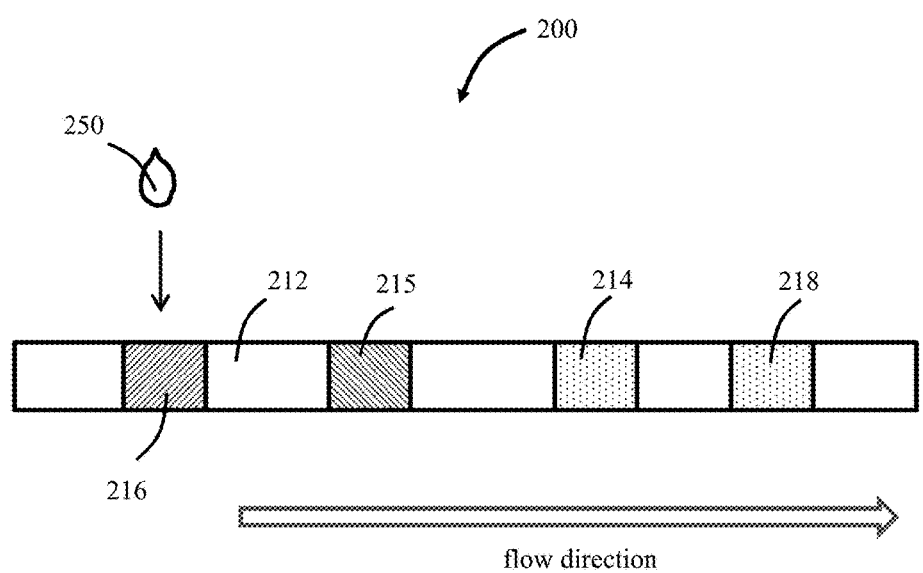
FIG. 1B illustrates a cross section of a diagnostic substrate 200 in accordance with some embodiments of the invention.

FIG. 1B illustrates a cross section of a diagnostic substrate 200 in accordance with some embodiments of the invention. The diagnostic substrate 200 can comprise a sample receiver 216 at least partially formed in or disposed on the diagnostic substrate 200 for receiving a sample 250, a reagent region 215 along the flow direction in the fluidic channel 212, a detection region 214, and optionally a control region 218. The flow direction is the moving direction of the sample 250 in the fluidic channel 212 as a result of capillary action.

The reagent region 215 can comprise one or more chemicals that react with or form complexes with an analyte in the sample 250. In accordance with some embodiments of the invention, the reagent region 215 can comprise a plurality of dyed nanoparticles with antibodies bound on the surface of the nanoparticles, the antibodies being specific to a target protein in the sample.

Calibration measurements performed in the control region 218 can be used to calibrate the measurements performed in the detection region 214. The control region 218 can equipped with a pair of light source and photodetector to perform the calibration measurements. The calibration measurement can be performed in both wet and dry states. This calibration step can reduce measurement errors due to sample-to-sample variation. In accordance with some embodiments of the invention, the calibrated transmission ($T_{calibrated}$) at the detection region 214 can be calculated using the following formula:

$$T_{calibrated} = \frac{T_{det\_wet} / T_{det\_dry}}{T_{cont\_wet} / T_{cont\_dry}},$$

where $T_{det\_wet}$ is the transmission value when the detection region is wet, $T_{det\_dry}$ is the transmission value when the detection region is dry, $T_{cont\_wet}$ is the transmission value when the control region is wet, $T_{cont\_dry}$ is the transmission value when the control region is dry.

Figure 1C:
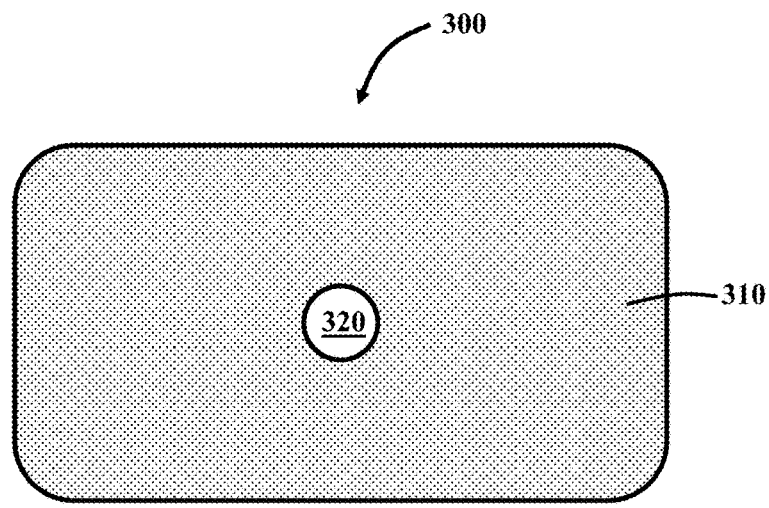
FIG. 1C illustrates a top-down view of a device 300.

The device 100 can further comprise a housing. FIG. 1C illustrates a device 300 that can enclose the device 100. The device 300 can comprise a housing 310 and an opening 320 for receiving a sample. The opening 320 can be aligned with the sample receiver 116 of the diagnostic substrate 110 such that the sample can contact with the diagnostic substrate 110.

The measurement devices described herein can be used to quantify the level of an analyte in a fluid sample. Without limitation, the fluid sample can be a biological sample, a chemical sample, or an environmental sample. The measurement devices described herein can be used to quantify the level of a target protein in a sample using ligand binding assays including, but not limited to, enzyme-linked immunosorbent assays (ELISA).

In accordance with some embodiments of the invention, the level of the target protein can be measured using a sandwich ligand binding assay. In these embodiments, the reagent region 215 of the diagnostic substrate can comprise a first antibody specific to the target protein or fragment thereof present in the sample. The first antibody can be present on the surface of a plurality of dyed nanoparticles. Once the target protein binds to the first antibody on the nanoparticles to form complexes, these complexes can then migrate along the flow direction to the detection region 214. The detection region can comprise a second antibody specific to the target protein. The second antibody can bind to the complexes and retain them in the detection region. Anything else that doesn't bind to the second antibody continues to migrate away from the detection region. The amount of the nanoparticles retained in the detection region is thus proportional to the level of the target protein. Other types of sandwich ligand binding assays can be used such as those involving enzymes and substrates.

In accordance with some embodiments of the invention, the level of a target protein can be measured using a competitive ligand binding assay. In these embodiments, the reagent region 215 of the diagnostic substrate can comprise a first antibody specific to the target protein or fragment thereof present in the sample. The first antibody can be present on the surface of a plurality of dyed nanoparticles. Once the target protein binds to the first antibody on the nanoparticles to form complexes, these complexes can then migrate along the flow direction to the detection region 214. The detection region can comprise a second antibody that can bind to the first antibody on the nanoparticles. This second antibody competes with the target protein for binding to the antibody on the nanoparticles. Only antibody/nanoparticle complexes that are not already bound to the target protein will bind to the second antibody. The amount of nanoparticles retained in the detection region is thus inversely related to the level of the target protein. Other types of sandwich ligand binding assays can be used such as those involving enzymes and substrates.

The devices described herein can also quantify the level of a target analyte in a sample based on a reaction involving the target analyte. In some of these embodiments, the reaction involving the target analyte can produce a compound that absorbs light at a particular wavelength. For example, alanine aminotransferase (ALT) can catalyzes the formation of pyruvate and glutamate from L-alanine and alpha-ketoglutarate. The pyruvate reacts to form hydrogen peroxide in the presence of pyruvate oxidase. Horseradish peroxidase, using hydrogen peroxide, then oxidizes 4-aminoantypyrine and N-ethyl-N-(2-hydroxy-3-sylfopropyl)-3,5-dimethoxyalanine to form a blue dye complex.

A change in transmissivity of the detection region can be used to quantify the level of an analyte in the sample. A first near-field communication (NFC) transaction by an external device (e.g., a wearable device such as a watch, a handheld device such as a smart phone) can initiate the measurement device described herein. After the measurement device is initiated, a dry calibration step is performed to measure light transmission at the detection region and the control region when it is dry. A user then contacts the sample receiver of the measurement device with a sample (e.g., blood, serum, urine, or saliva). The measurement device can continuously or intermittently measure light transmission at the detection region and the control region. In accordance with some embodiments of the invention, the measurement device can measure light transmission at the detection region and the control region at two or more predetermined time periods after the contacting (e.g., about 1-30 minutes). Data obtained in these measurements can be stored in the data storage device.

In accordance with some embodiments of the invention, each of the transmission measurements can be done with either the constant-input or constant-output modes. Using either the constant-input or constant-output modes of operation of the measurement device, the signal may vary monotonically and repeatably with the transmissivity change, for example as shown in the examples shown in FIGS. 2A and 2B. Electromagnetic waves from the electromagnetic radiation source pass through and/or scatter from the color-sensitive region of the measurement device to reach the detector. In this non-limiting example, the electromagnetic radiation source is depicted as a LED, and the detector is depicted as a photodetector. In other examples, other types of excitation sources and detectors can be used.

According to the example systems, methods and apparatus herein, a change in transmissivity of a portion of the measurement device (such as but not limited to a membrane) can be read more accurately to quantify the underlying biochemistry. The properties of the example systems are tailored so that the changes in transmissivity span the entire sensitive range of the electronic system. The two non-limiting example methods of measuring the change in transmissivity using an LED and a photodetector placed on opposite sides of the membrane are described in connection with FIGS. 2A and 2B.

Figure 2A:
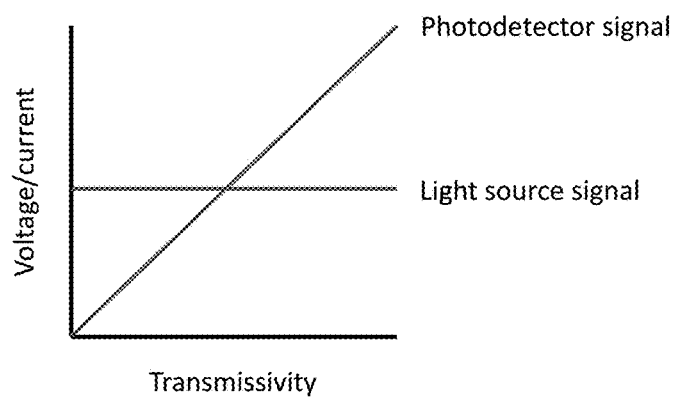
FIG. 2A is a graph illustrating constant-input mode of operation of the measurement device. The LED signal is kept constant, and the photodetector (PD) signal, which increases with transmissivity, is the output value. When transmissivity is high, so is the PD signal.

In FIG. 2A, the LED signal is kept substantially constant and the photodetector signal (shown as PD Signal) is the measured output value. For example, a constant current is provided to the LED, and the voltage measured at the photodetector is used as a measure of transmissivity. The PD Signal is shown to increase with increasing transmissivity in this example. While the plot is shown as linear, in other examples, the detector response may be curved, monotonically increasing, or plateau (due to signal saturation). When transmissivity is high, the PD signal is also high. This example method can be implemented when the transmissivity is high, but not when it is low, since the signal at the photodetector may approach the noise floor.

Figure 2B:
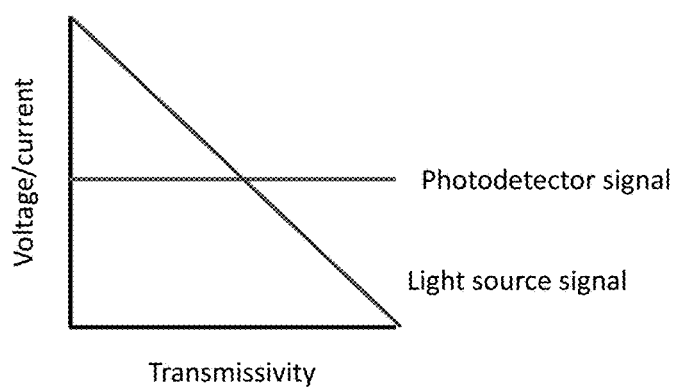
FIG. 2B is a graph illustrating constant-output mode of operation of the measurement device. The PD signal is kept constant, and the LED signal, which decreases with transmissivity, is the output value. When the transmissivity is low, the LED signal is high.

In FIG. 2B, the PD signal is kept substantially constant, and the LED signal is the measured output value. For example, the current provided to the LED is varied to generate a constant voltage as measured at the photodetector, and the current to the LED is used as a measure of transmissivity. The LED Signal is shown to decrease with increasing transmissivity in this example. When transmissivity is low, the LED signal is high. This example method can be implemented when the transmissivity is low, but not when it is high, since the current used to drive the LED may approach the noise floor.

In an example, the methods described in connection with FIG. 2A and/or FIG. 2B may be combined in a single measurement session of use of a measurement device to facilitate more accurate measurements of transmissivity over the entire range of the detection system.

According to the example systems, methods and apparatus herein, the appropriate mode is selected based on the transmissivity and the type of assay, and allows measurement of a relatively large signal over substantially the entire range of measured output values of the detection system.

These example methods place no restriction on how to choose which method to use in a given circumstance. In an example implementation, the methods described in connection with FIG. 2A may provide more accurate results for measurements at higher values of transmissivity, and the method described in connection with FIG. 2B may provide more accurate results for measurements at lower values of transmissivity. There is a mid-range of transmissivity over which the method described in connection with FIG. 2A or FIG. 2B may be used.

The methods described in connection with FIG. 2A and/or FIG. 2B can be combined with other methods for improving accuracy, such as but not limited to measuring the transmissivity using multiple input currents and/or output voltages, and/or measuring the change in transmissivity over time as the assay progresses.

In an example, the methods described in connection with example FIG. 2A and/or FIG. 2B may be combined in a single measurement session to provide multiple measurement modalities that facilitate keeping the measurements well above the electrical noise floor of the detection system over the entire range of transmissivity, so that electrical and quantization noise do not contribute significantly to the overall measurement noise.

Figure 3:
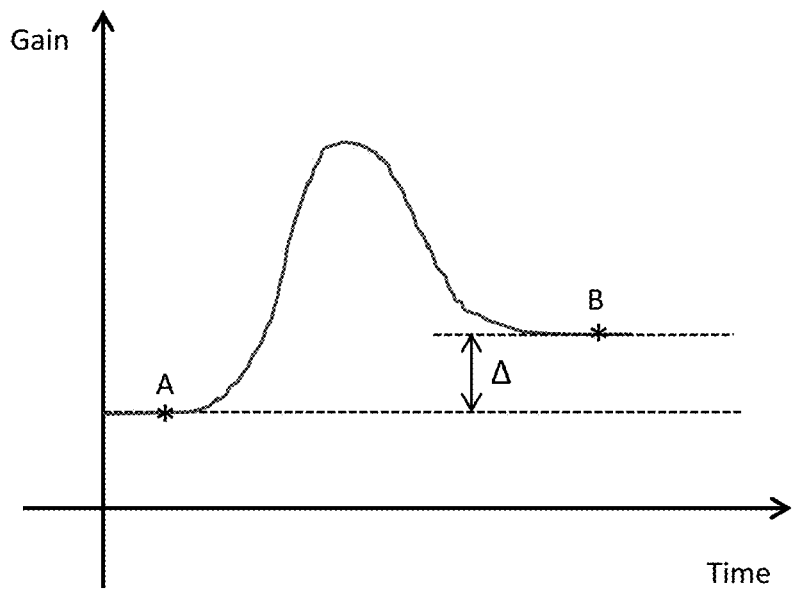
FIG. 3 is a graph illustrating how the level of an analyte in a sample can be quantified.

In accordance with some embodiments of the invention, each of the transmission measurements can be done by recording the photodetector output as a function of increasing light intensity from the light source. Stated another way, the light source gradually increases the light intensity during each of the transmission measurements, and the photodetector detects light transmission in response to the increase in light intensity. The relationship between the light intensity of the light source (or the current of the light source) and the photodetector output can be used to derive a value termed "gain" herein. A relation between gain and time can be used to quantify the level of the target analyte. FIG. 3 shows an example graph of the temporal change in the values of gain. Point A indicates that the detection region is dry (i.e., prior to the detection region in contact with the sample). Point B indicates a steady state when the level of the target analyte in the detection region has stabilized. The level of the target analyte can be extract from the difference in gain between point A and point B. The data stored in the data storage device can be transmitted to the external device through a second NFC transaction. The external device can analyze the data and present quantitative information about the sample (e.g., level of the analyte).

In a non-limiting example implementation, the measurement device can be used to analyze a sample of biological origin, such as but not limited to blood. The data collected from the measurement device can be analyzed to detect the presence of, or lack of, certain nutrients in blood. For example, a sample, such as but not limited to a drop of blood, may be taken from a subject or from another stored source, and is analyzed using an assay or other chemical present on, or introduced to, the measurement portion of the example measurement device. In another example, the sample may be processed prior to introduction to the measurement portion of the example measurement device. A blood sample may be filtered to derive blood plasma; the blood plasma is introduced to the measurement portion of the example measurement device. The data collected from the measurement device can be analyzed to detect HIV, malaria, or used to evaluate the level of cholesterol or of micronutrients such as but not limited to iron, zinc, iodine, and vitamin A levels.

An example measurement device according to the principles herein may be configured as a low-cost glucose reader that does not need an on-board power source. A blood sample or a sample derived from blood may be introduced to a designated portion of the example glucose reader that includes the analytes for the glucose level analysis. According to the principles described herein, processor-executable instructions (including an application software) may be configured to provide an indication to a user when sufficient time has passed for the reaction analysis to be completed. Furthermore, the data readout capability need not be integrated with the example glucose reader device. The example glucose reader may be configured to transmit data, e.g., using a communication protocol, to the computing device or other data storage or when sufficient time has passed for a retrieval system. In some embodiments, the example glucose reader may be disposable, or re-usable for a limited number of uses or for a limited period of times (e.g., for about two weeks or about a month). The low-cost, disposable glucose reader may include multiple channels, each of which can be used to analyze blood samples to provide a glucose level measurement.

In accordance with some embodiments of the invention, the analyte is ferritin. Ferritin is a protein found inside cells that stores iron. Ferritin levels can indicate the amount of iron in a subject's blood. In accordance with some embodiments of the invention, the analyte is retinol binding protein (RBP). RBP levels can indicate the amount of vitamin A. In accordance with some embodiments of the invention, the analyte is a C-reactive protein (CRP). High CRP levels are known to indicate inflammation. Non-limiting examples of other analytes include cholesterol, iodine, troponin, and other proteins. In accordance with some embodiments of the invention, the analyte is alanine aminotransferase (ALT).

ALT is typically measured to see if the liver is damaged or diseased. Low levels of ALT are normally found in the blood. But when the liver is damaged or diseased, it releases ALT into the bloodstream, which makes ALT levels go up.

An example measurement device according to the principles herein may be configured for detection of troponin levels in a sample. In an example, the sample can be a blood sample or derived from a blood sample. Increased troponin levels, even merely a detectable amount, in the sample can serve as a biomarker of damage to heart muscle or a heart disorder, such as but not limited to myocardial infarction. For example, even small increases in troponin levels can serve as an indicator of cardiac muscle cell death. As a non-limiting example, this implementation can be used to determine if chest pains are due to a heart attack. Using the example measurement device, the troponin levels can be quantified, and based on an analysis of the measurements, it can be determined whether the troponin levels are indicative of myocardial necrosis consistent with myocardial infarction. The analysis can be performed using a processor of the example measurement device or using a processor of an external computing device.

According to the principles described herein, processor-executable instructions (including an application software) may be configured to provide an indication to a user when sufficient time has passed for the reaction analysis to be completed. The example measurement device may be configured to transmit data, e.g., using a communication protocol, to the computing device or other data storage or when sufficient time has passed for a retrieval system.

In an example implementation, the example measurement device can be configured for providing quantitative information relating to a sample. The example measurement device can include a substrate that has at least one paper-based portion, a sample receiver at least partially formed in or disposed on a paper-based portion of the substrate, and electronic circuitry. The electronic circuitry is at least partially formed in or disposed on the substrate. The electronic circuitry generates an analysis result based on an output signal from the sample or a derivative of the sample.

Quantitative information from analysis of a sample can be used for, e.g., determining glucose levels, or diagnosing diseases, e.g., HIV, malaria, etc. When a sample, such as but not limited to blood, is placed onto the measurement device described herein, a pre-deposited assay can be used to analyze the sample. As non-limiting examples, a measurement platform based on the example measurement devices described herein can be configured to provide data or other information indicative of at least one constituent of the sample. In an example, the data or other information can be stored to a memory of the measurement device or transmitted wirelessly. In another example, the measurement platform based on the example measurement devices described herein can be configured to provide an indication of the data or other information from the quantitative measurements, such as but not limited to a change in a color indication, a symbol, and/or a digital readout. The results of the quantitative measurements can be used to provide an indication of a condition of an individual, such as but not limited to, a glucose level or an indication of vitamin D level, or a positive or negative indication for an affliction (such as but not limited to HIV or malaria), and/or a degree of progression of an affliction. In some examples, the devices can be configured for performing electrical quantitative measurements that can be used for medical diagnosis, including determining the presences of and/or quantifying, proteins or antibodies, such as but not limited to a malaria diagnosis or a HIV diagnosis.

The measurement devices can be fabricated using methods known in the art. For example, the electronic circuitry and other components can be formed over the paper in a printing process. Microfluidic devices may be constructed, for example, using techniques developed by Martinez et al: Proc. Natl. Acad. Sci. USA 105, 19606-11 (2008); Lab. Chip. 8, 2146-50 (2008); and Angew. Chem. Int. Ed. Engl. 46, 1318-20 (2007), each of the references being herein incorporated by reference in its entirety. Micro-LEDs and Micro-photodiodes are both commercially available.

To form an integrated electronic and microfluidic device, an appropriate patterned-paper platform for the device can be designed and developed. The paper-based substrate can be selected based on wicking speeds, sample retention, consistency and compatibility with the required assay (e.g., glucose oxidase). Biocompatible excipients such as sucrose or trehalose may be used to stabilize enzymes used in the assay. Plasma separation membranes can be also selected for the desired diagnostic.

Many other substrates may be used for creating a microfluidic device or device layers. Device layers may be composed of a variety of semi-permeable materials such as porous polymers and elastomers, rigid or flexible nanofiber composites, biologically selective membranes (e.g., fluid mosaic model). Other materials that may facilitate a wicking effect similar to paper can also be used. These materials may include gels with wicking properties, and electromagnetic materials that may be designed to create peristaltic motions to pulse analytes and other fluids to test wells.

In any example according to the principles herein, the measurement device can be configured as flexible conformal electronic devices with modulated conformality. The control over the conformality allows the generation of measurement devices that can be conformed to the contours of a surface without disruption of the functional or electronic properties of the measurement device. The conformality of the overall conformal device can be controlled and modulated based on the degree of flexibility and/or stretchability of the structure. Non-limiting examples of components of the conformal electronic devices include a processing unit, a memory (such as but not limited to a read-only memory, a flash memory, and/or a random-access memory), an input interface, an output interface, a communication module, a passive circuit component, an active circuit component, etc. In an example, the conformal electronic device can include at least one microcontroller and/or other integrated circuit component. In an example, the conformal electronic device can include at least one coil, such as but not limited to a near-field communication (NFC) enabled coil. In another example, the conformal electronic device can include a radio-frequency identification (RFID) component.

Another aspect of the invention relates to a timer or other counter mechanism built into a measurement device, e.g., the measurement devices described above. According to the example systems, methods, and apparatus described herein, technology is provided for activation of example measurement devices. As a non-limiting example, the example activation of the example measurement devices can be based on detection of an amount of a sample disposed on a receiver portion of the example quantitative measurement devices. For example, the example measurement devices can be configured for detecting a colorimetric change, a change in electrical conductivity, or other quantifiable change, due to the other detection and/or quantification of at least one constituent of the sample, such as but not limited to a biological sample or other chemical sample. The colorimetric change can be detected, e.g., by the use of a light source and a photodetector. The change in electrical conductivity can be detected, e.g., by the detection of an electrical current above a certain threshold.

In accordance with some embodiments of the invention, a measurement device equipped with a timer is provided herein, the device comprising (a) a sample receiver for receiving a sample; (b) a sensor coupled to the sample receiver to detect the presence of the sample; (c) a detection region fluidly coupled to the sample receiver via a fluidic channel, thereby receiving the sample or a derivative thereof from the sample receiver; (d) a detector coupled to the detection region and configured to read a characteristic of the sample or the derivative thereof; and (e) a timer coupled to the sensor and the detector, wherein the timer is activated for a predetermined time when a sample is detected, the predetermined time representing the amount of time to read the sample, the timer activating the detector after the predetermined time has been reached, the detector outputting a measurement value.

In accordance with some embodiments of the invention, a change in transmission detected by the sensor indicates the presence of the sample. In some of these embodiments, the sensor comprises a light source and a photodetector.

In accordance with some embodiments of the invention, a change in electrical conductivity detected by the sensor indicates the presence of the sample. In some of these embodiments, the sensor comprises electrical components connected to the sample receiver in the sample receiver. For example, the addition of a sample in the sample receiver can result in a current in the electronic circuit, indicating the presence of the sample.

In accordance with some embodiments of the invention, the measurement device further comprises a communications interface coupled to the sample receiver, the communications interface receiving a command signal from an external device to initiate the accepting of the sample.

In accordance with some embodiments of the invention, the sensor is deactivated after the predetermined time.

According to the example systems, methods, and apparatus described herein, technology is provided for start of a measurement that facilitates obtaining an accurate reading of a measurement device, by controlling the duration of a measurement via automated monitoring of start and stop times. The example systems, methods, and apparatus described herein may be used with, but do not require, user intervention or other input via a start button or a software controlled start using a mobile application on a phone. The example systems, methods, and apparatus described herein exploit the physics of the effect of disposing a sample at a receiver, such as but not limited to dropping blood into a microfluidic channel, to determine the start of monitoring the time it would take to get an accurate measurement result.

The example systems, methods, and apparatus described herein facilitate better accuracy, eliminate or significantly reduce the chance of user error, and/or make a measurement device easier to use.

Any of the example methods according to the principles described herein may be implemented using a quantitative device that includes electronic components or other components that can be used to poll the receiver according to a pre-set schedule and/or at regular time intervals for detecting whether an amount of the sample is disposed at the receiver of the example measurement device according to the principles described herein. An indication of the presence of a sample at the receiver can be transmitted or otherwise communicated to other components of the measurement device.

Any of the example methods according to the principles described herein may be implemented using a measurement device that includes electronic components to receive the indication of the presence of a sample at the receiver, and to cause a timer or other counter mechanism to be activated. The example timer or other counter mechanism may be pre-set to monitor the amount of time (T1) it is expected to take for the assay at the receiver and one or more analytes in the sample to react and generate a result. The result may be any change that may be measured, including any colorimetric change and/or electrical change.

According to the example systems, methods, and apparatus described herein, the receiver of the example measurement device can be coupled to a microfluidic channel or other conduit that leads from the receiver to a reservoir of the example measurement device. In an example, the receiver can be configured as a sample well or other receptacle. At least a portion of the sample can flow or otherwise travel from the receiver to the reservoir via the microfluidic channel or other conduit. The reservoir can include an assay to react with the portion of the sample reaching the reservoir. Measurement and/or analysis of the reaction at the reservoir can provide data or other quantifiable information indicative of at least one constituent of the sample.

In an example, re-usable low-cost systems, with reduced operating costs, can be produced using the example systems, methods, and apparatus described herein. In other examples, at least a portion of the example measurement device can be disposable. For example, the receiver and/or the microfluidic channel or other conduit may include at least one paper-based portion and/or at least one polymer-based portion.

In another example, an example timer or other counter mechanism can be configured to monitor an amount of time (T2) it is expected to take for at least a portion of the sample to flow or otherwise travel from the receiver to the reservoir, and/or an amount of time (T3) for at least a portion of a reaction to occur at the reservoir between the assay at the reservoir and the portion of the sample to reach the reservoir. The example timer or other counter mechanism can be triggered to commence monitoring time interval T2 and/or T3 based on the indication of the presence of blood or other sample at the receiver.

According to the example system, method or apparatus herein, the measurement device can be configured to operate automatically to measure an amount of an analyte in a sample without input from the user. For example, once an amount of a sample is disposed at the receiver, the example measurement device can be configured to automatically detect the change, including the colorimetric or electrical change, at the receiver based on the presence of the sample. The example measurement device can be configured to automatically commence a timer (or other counter mechanism). The example timer (or other counter mechanism) can be pre-set to monitor, e.g., the amount of time (T2) it is expected to take for at least a portion of the sample to flow or otherwise travel from the receiver to the reservoir, and/or the amount of time (T3) it is expected for at least a portion of a reaction to occur at the reservoir between the assay at the reservoir and the portion of the sample to reach the reservoir. Once the expected interval of time is reached, the example measurement device can be configured to automatically perform a measurement, such as but not limited to a measurement of the results of the reaction occurring at the reservoir between the assay at the reservoir and the portion of the sample. Accordingly, user input is not required to trigger any component of the example measurement device based on the elapse of time period T1, T2, and/or T3. In any example implementation, the measurement device can be configured to invite user input, including user input to trigger any component.

Figure 13:
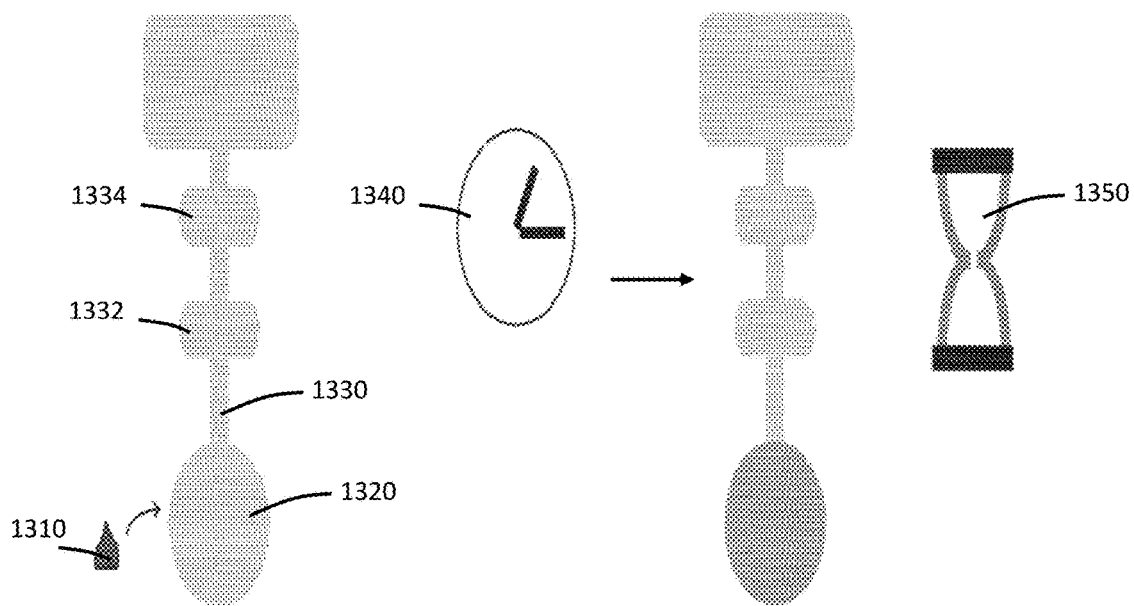
FIG. 13 is an illustration showing an example sequence of operation of the example measurement device.

FIG. 13 shows an example sequence of operation of the example measurement device. An amount of blood or other sample 1310 is disposed on the receiver 1320. The example receiver 1320 may be coupled to a fluidic channel 1330 that includes a measurement line 1332 and optionally a control line 1334. A component 1340 of the measurement device is used to poll according to a pre-set schedule and/or at regular time intervals to determine if the blood or other sample 1310 is disposed on the receiver 1320. The reaction of the assay present at the receiver 1320 with one or more analytes in the sample may cause a change, such as but not limited to a colorimetric change and/or an electrical change. The polling performed can include determining from a signal at a component of the system whether the colorimetric, electrical and/or other change is detected at the receiver 1320. The example measurement device may be configured such that electronic components that are not involved in the polling or the quantification of the change at the receiver 1320 may be kept in a dormant state, or in an OFF state, to conserve power. On receiving an indication of the presence of blood or other sample at receiver 1320, at least one pre-set timer (or other counter mechanism) 1350 can be activated. The at least one timer (or other counter mechanism) 1350 may be set to monitor any amount of time (T) it is expected to take for the assay and analyte to react and generate result. Any change, including any colorimetric change and/or any electrical change, may be measured. In other examples, the at least one timer (or other counter mechanism) 1350 may be set to monitor any time period T1, T2, and/or T3, according to any of the principles described herein.

Figure 14:
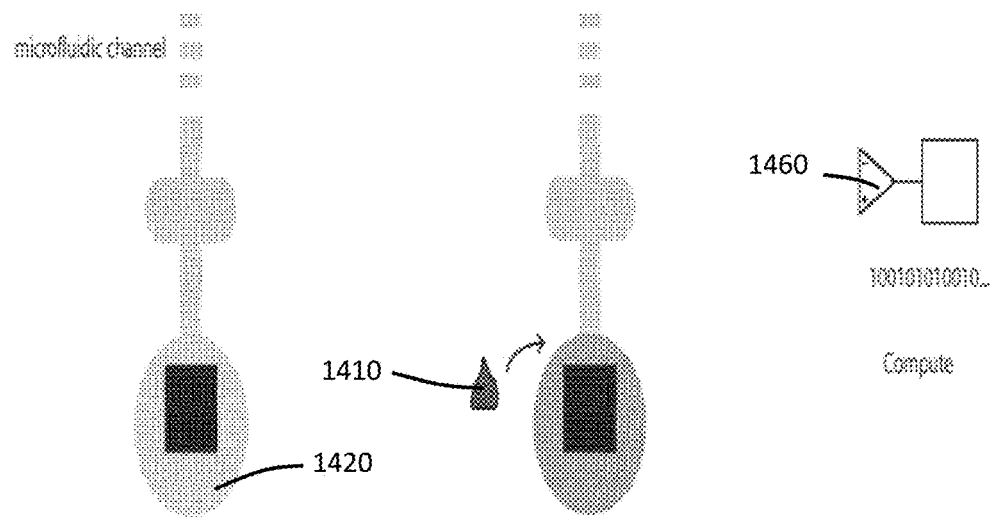
FIG. 14 is an illustration showing an example implementation where a colorimetric change at the receiver 1420 is used for detecting the presence of the sample 1410 at the receiver 1420.

FIG. 14 shows an example implementation where a colorimetric change at the receiver 1420 is used for detecting the presence of the sample 1410 at the receiver 1420. When no blood or other sample 1410 is disposed at the receiver 1420, the color and/or opacity of the receiver 1420 is based on, e.g., the substrate of the receiver 1420 and any analyte of the assay present at the receiver 1420. The measurement device may include an electromagnetic radiation source, such as but not limited to a LED, to illuminate at least a portion of the receiver 1420. A detector, such as but not limited to a photodetector, can be used to measure the intensity, electromagnetic wavelength(s), or other quantifiable measure of the receiver 1420 in the absence of blood or other sample. When an amount of blood or other sample is disposed at the receiver 1420, the color and/or opacity at the receiver 1420 is configured to change. The electromagnetic radiation source, such as but not limited to a LED, is used to illuminate at least a portion of the receiver 1420. The detector, such as but not limited to the photodetector, can be used to measure any difference in the intensity, electromagnetic wavelength(s), or other quantifiable measure of the receiver 1420 based on the presence of the blood or other sample. A comparison 1460 is made to determine whether the difference in measured data is based on the presence of blood or other sample 1410 at the receiver 1420. Based on the result of the comparison, at least one timer (or other counter mechanism) can be caused to start monitoring a time interval for triggering another component. For example, the timer (or other counter mechanism) can be caused to start a state machine for measuring the analyte/assay that arrives at the reservoir. In an example, the measurement device may include an analysis engine to perform the comparison. In another example, the data indicative of the measurements may be communicated to an external computing device to perform the comparison.

In an example, the presence of the sample at the receiver may cause a color change or an opacity change (increasing or decreasing translucence), or other colorimetric change at the receiver. The measurement device can be configured to poll the receiver intermittently or at regular time intervals to determine whether a colorimetric change has occurred at the receiver. The polling can involve intermittent powering up of the illumination source to illuminate using electromagnetic radiation and powering up of a detector to detect the optical properties at the receiver from the illumination. If no change is detected, the components can be cause to return to an OFF or dormant state. If the colorimetric change at the receiver is detected, one or more other electronic components of the measurement device may be activated or powered up to perform other operations, such as but not limited to measurement of a result of a reaction at the reservoir after an interval of time pre-set at a timer or other counter mechanism, or an interval of time determined based on the quantification of the colorimetric change at the receiver. The data indicative of the measurement at the reservoir may be stored to a memory of the measurement device or transmitted to an external computing device.

Figure 15:
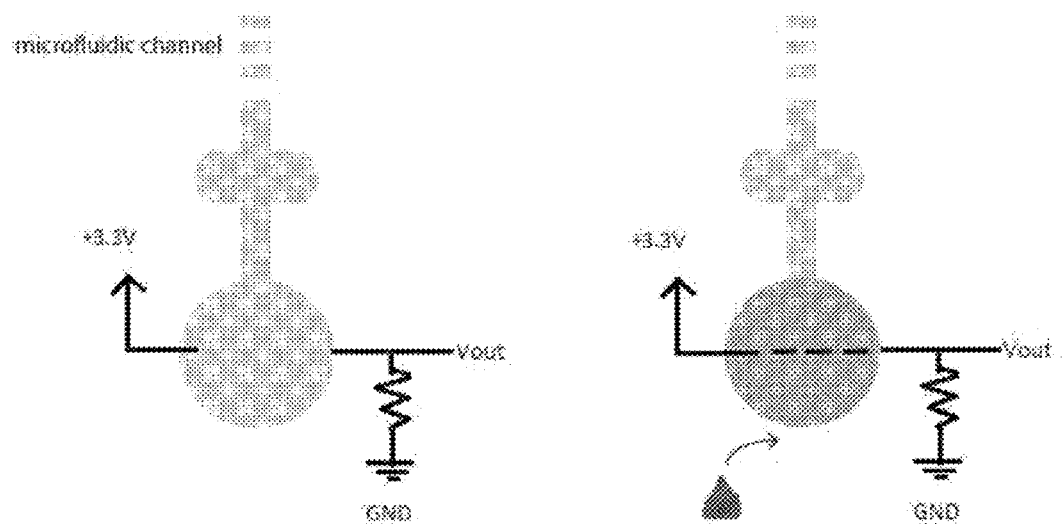
FIG. 15 is an illustration showing an example implementation in a system where an electrical change at the receiver is used for detecting the presence of the sample at the receiver.
Figure 16:
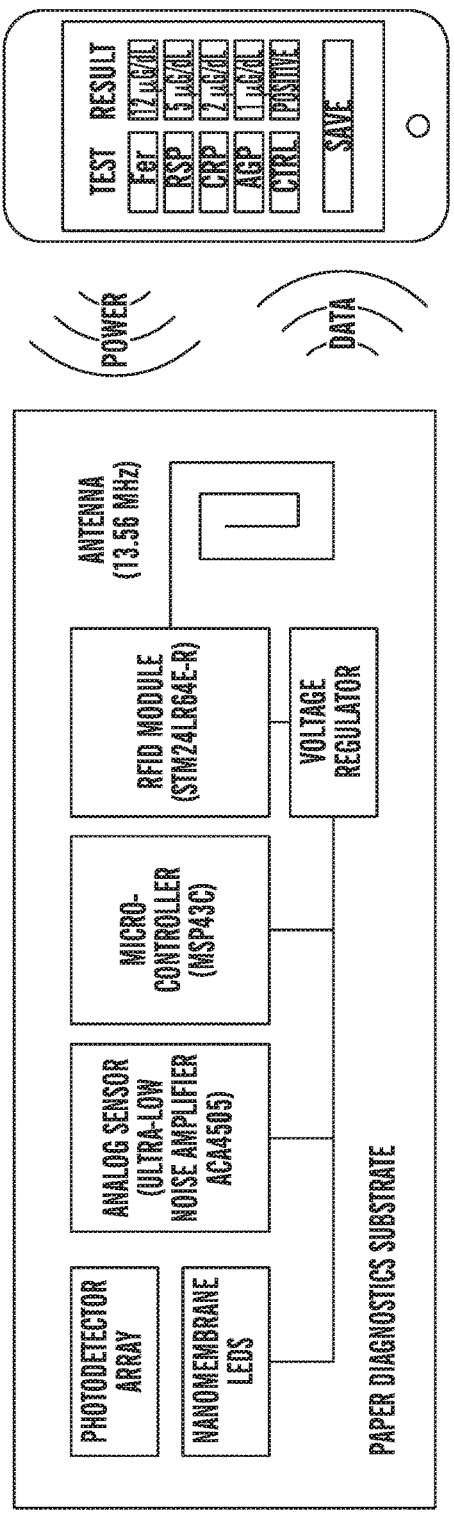
FIG. 16 is a block diagram highlighting key modules involved in sensing, analog data amplification, sampling and transmission to NFC enabled smart phone. The voltage regulator stores power collected from smart phone, sufficient to drive LEDs, photodetectors and associated circuitry.

FIG. 15 shows an example implementation in a system where an electrical change at the receiver is used for detecting the presence of the sample at the receiver. The measurement device can be configured such that, when no blood or other sample is present at the receiver, there is no electrical path, e.g., from one portion of the receiver to another. For example, in the absence of or other sample at the receiver, there is no electrical path for a current to go from the higher voltage side (in the example of FIG. 15, about +3.3V) to the lower voltage side (in this example, the $V_{out}$). In the example of FIG. 15, there is a path from ground (GND) so the $V_{out}$ is grounded. The measurement device can be configured such that, when an amount of blood or other sample is disposed at the receiver, an electrical path is created, e.g., from one portion of the receiver to another. For example, when the blood or other sample is disposed at the receiver, the salinity or other conductive component of the blood or other sample allows current to flow across the receiver (e.g., across the blood or other sample and a portion of a membrane of the receiver). The change in the electrical (including impedance) properties of the receiver can be measured to indicate the presence of the blood or other sample. For example, based on an appropriate choice of a resistor, $V_{out}$ can be made to approach about 3.3V, which can be measured. In another example, the change can be determined based on a comparison of the measured value of the electrical properties of the receiver in the absence of the sample to the measured value of the electrical properties of the receiver in the presence of the sample.

In an example, the presence of the sample at the receiver may cause a change in electrical property at the receiver, using an impedance measurement. For example, a difference in electrical property can be measured as an indicator of a difference in impedance at a portion of the reservoir to indicate the presence of electrolytes in the sample. The measurement device can be configured to poll the receiver intermittently or at regular time intervals to determine whether a change in electrical properties has occurred at the receiver. The polling can involve intermittent powering up of a voltage source to apply a potential difference across a portion of the receiver, and an impedance measurement can be performed. If no change in impedance is detected, the components can be caused to return to an OFF or dormant state. If the impedance change at the receiver is detected, one or more other electronic components of the measurement device may be activated or powered up to perform other operations, such as but not limited to measurement of a result of a reaction at the reservoir after an interval of time pre-set at a timer or other counter mechanism, or an interval of time determined based on the quantification of the colorimetric change at the receiver. The data indicative of the measurement at the reservoir can be stored to a memory of the measurement device or transmitted to an external computing device.

In any of the example measurement devices according to the systems, methods, and apparatus described herein, data indicative of a reaction of an assay with an analyte, or any other data, may be transmitted to a memory of the system and/or communicated (transmitted) to an external memory or other storage device, a network, and/or an off-board computing device. In any example herein, the external storage device can be a server, including a server in a data center. Non-limiting examples of a computing device applicable to any of the example systems, apparatus or methods according to the principles herein include smartphones, tablets, laptops, slates, e-readers or other electronic reader or hand-held or worn computing device, an Xbox®, a Wii®, or other game system(s).

Any of the example measurement devices according to the systems, methods, and apparatus described herein can be configured for intermittent use.

Any of the example measurement devices according to the systems, methods, and apparatus described herein can be configured as sensor units, sensor patches, diagnostic devices, or any other measurement device that can be operated as described herein. As a non-limiting example, the example measurement device can be a glucose monitor or other glucose measurement device.

According to the example systems, methods, and apparatus described herein, the devices can be configured for many different types of sensing modalities. Non-limiting example sensing modalities include detecting and/or quantifying pressure, impedance, capacitance, blood flow and/or the presence of specific substances, such as but not limited to chemicals, proteins, or antibodies. In some examples, the devices can be implemented for performing electrical measurement of environmental condition(s).

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

Some embodiments of the invention are listed in the following numbered paragraphs:

1. A measurement device comprising:
a diagnostic substrate comprising (a) a sample receiver to receive a sample, wherein the sample receiver is at least partially formed in or disposed on the diagnostic substrate; (b) a fluidic channel connected to the sample receiver; (c) a detection region at least partially formed in or disposed on the diagnostic substrate, wherein the detection region is coupled to the sample receiver by the fluidic channel; (d) a control region at least partially formed in or disposed on the diagnostic substrate, wherein the control region is coupled to the detection region by the fluidic channel, and
a base substrate comprising (e) an antenna for near-field communication (NFC) at least partially formed in or disposed on the base substrate; (f) electronic circuitry connected to the antenna and at least partially formed in or disposed on the base substrate, wherein the electronic circuitry generates data as a function of an output signal from the sample or a derivative thereof; (g) a first portion comprising a first photodetector and a second photodetector connected to the electronic circuitry and at least partially formed in or disposed on the first portion; (h) a second portion comprising a first light source and a second light source connected to the electronic circuitry and at least partially formed in or disposed on the second portion, wherein the first portion and the second portion are positioned to align the photodetectors and the light sources such that light from the first light source passes through the detection region and gets detected by the first photodetector, the light from the second light source passes through the control region and gets detected by the second photodetector, and (i) a thin-film battery connected to the electronic circuitry and configured to provide power to the at least one photodetector and light source.

2. The measurement device of paragraph 1, wherein the diagnostic substrate further comprises a reagent to react with the sample or the derivative of the sample.

3. The measurement device of paragraph 2, wherein the reagent is a plurality of dyed nanoparticles.

4. The measurement device of paragraph 1, further comprising a data storage device connected to the electronic circuitry and configured to store the data.

5. The measurement device of paragraph 1, further comprising a sensor coupled to the sample receiver to detect the presence of the sample.

6. The measurement device of paragraph 5, wherein the sensor is polled periodically or according to a pre-set schedule to determine the presence of the sample.

7. The measurement device of paragraph 5, further comprising a timer coupled to the sensor and the photodetector, wherein the timer is activated for a predetermined time when the sample is detected, the predetermined time representing the amount of time to read the sample, the timer activating the photodetector after the predetermined time has been reached, the photodetector outputting a measurement value.

8. The measurement device of paragraph 7, wherein the sensor is deactivated after the predetermined time.

9. The measurement device of paragraph 1, further comprising a housing for enclosing at least a portion of the measurement device.

10. The measurement device of paragraph 1, wherein the measurement device is initiated by an external device through a first NFC transaction.

11. The measurement device of paragraph 10, wherein the measurement device transmits the data to the external device through a second NFC transaction, whereby the external device processes the data to provide quantitative information related to the sample.

12. The measurement device of paragraph 10 or 11, wherein the external device is a hand-held device or a wearable device.

13. The measurement device of paragraph 11, wherein the quantitative information comprises at least one of: a glucose level; a T-cell concentration; a microorganism concentration; a water-based pathogen concentration; a bovine serum albumin (BVA) concentration; a bacterial concentration; a viral load; an antigen level; an antibody level; a diagnosis of tuberculosis; a diagnosis of dengue fever; a cardiac enzyme concentration; and a diagnosis of malaria.

14. The measurement device of paragraph 1, wherein the first portion is folded over the second portion such that the first portion and the second portion sandwich the diagnostic substrate.

15. The measurement device of paragraph 1, wherein the second portion is folded over the first portion such that the first portion and the second portion sandwich the diagnostic substrate.

16. The measurement device of paragraph 1, wherein the sample is a fluid sample.

17. The measurement device of paragraph 16, wherein the fluid sample is selected from the group consisting of blood, serum, saliva, and urine.

18. The measurement device of paragraph 1, wherein the diagnostic substrate comprises a paper-based portion.

19. A measurement device for measuring a value from a sample, the device comprising:
a sample receiver for receiving a sample;
a sensor coupled to the sample receiver to detect the presence of the sample;
a detection region fluidly coupled to the sample receiver via a fluidic channel, thereby receiving the sample or a derivative thereof from the sample receiver;
a detector coupled to the detection region and configured to read a characteristic of the sample or the derivative thereof; and
a timer coupled to the sensor and the detector, wherein the timer is activated for a predetermined time when a sample is detected, the predetermined time representing the amount of time to read the sample, the timer activating the detector after the predetermined time has been reached, the detector outputting a measurement value.

20. The device of paragraph 19, wherein the sample is a fluid sample.

21. The device of paragraph 19, wherein the sensor comprises a light source and a photodetector, wherein the light source and the photodetector are positioned such that light from the light source passes through the sample receiver and gets detected by the photodetector.

22. The device of paragraph 21, wherein a change in transmission detected by the sensor indicates the presence of the sample.

23. The device of paragraph 19, wherein the sensor comprises electrical components configured to detect an electrical signal from the sample.

24. The device of paragraph 23, wherein a change in electrical conductivity detected by the sensor indicates the presence of the sample.

25. The device of paragraph 19, wherein the sensor is polled periodically or according to a pre-set schedule to determine the presence of the sample.

26. The device of paragraph 19, wherein the sensor is deactivated after the predetermined time.

27. The device of paragraph 19, further comprising a communications interface coupled to the sample receiver, the communications interface receiving a command signal from an external device to initiate the accepting of the sample.

28. The device of paragraph 27, wherein the external device is a hand-held device or a wearable device.

29. The device of paragraph 19, further comprising a data storage device coupled to the detector, the detector storing the measured value in the data storage device.

30. The device of paragraph 27, wherein the communications interface sends a signal indicative of the measured value.

31. The device of paragraph 20, wherein the fluid sample is selected from the group consisting of blood, serum, saliva, and urine.

32. A method of providing quantitative information on a sample using a measurement device of paragraph 1, the method comprising:
(i) initiating the measurement device with an external device through a first near-field communication (NFC) transaction, wherein the measurement device performs a first transmission measurement on the detection region and the control region to produce a first data;
(ii) contacting the sample receiver of the measurement device with the sample, wherein the measurement device performs a second transmission measurement on the detection region and the control region at a first predetermined time period after the contacting to produce a second data;
(iii) performing a third transmission measurement on the detection region and the control region at a second predetermined time period after the second transmission measurement to produce a third data;
(iv) transferring the first, second, and third data from the measurement device to the external device through a second NFC transaction; and
(v) providing quantitative information based on analysis of the first, second, and third data.

33. The method of paragraph 32, wherein the sample is a fluid sample.

34. The method of paragraph 32, wherein the analysis comprises normalizing the third data against the first and second data.

35. The method of paragraph 32, further comprising storing the first, second, and third data in a data storage device prior to the transferring.

36. The method of paragraph 32, wherein the external device is a hand-held device or a wearable device.

37. The method of paragraph 32, wherein the quantitative information comprises at least one of: a glucose level; a T-cell concentration; a microorganism concentration; a water-based pathogen concentration; a bovine serum albumin (BVA) concentration; a bacterial concentration; a viral load; an antigen level; an antibody level; a diagnosis of tuberculosis; a diagnosis of dengue fever; a cardiac enzyme concentration; and a diagnosis of malaria.

38. The method of paragraph 33, wherein the fluid sample is selected from the group consisting of blood, serum, saliva, and urine.

39. The method of paragraph 32, wherein the first and second light sources each gradually increases the light intensity during each of the transmission measurements, and the first and second photodetectors each detects light transmission in response to the increase in light intensity.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

The term "NFC" refers to near field communication, a short-range, high frequency wireless communication technology that enables the exchange of data between devices over about a small (e.g. 20 centimeter or less) distance.

The term "analyte" is used herein to refer to a substance or chemical constituent in a sample (e.g., a biological or industrial fluid) that can be analyzed (e.g., detected and quantified) and monitored using the measurement devices described herein. Examples of an analyte include, but are not limited to, a small inorganic or organic molecule, an ion, a nucleic acid (e.g., DNA, RNA), a protein, a polypeptide, a peptide, a monosaccharide, a polysaccharide, a metabolic product, a hormone, an antigen, an antibody, a biological cell, a virus, and a liposome.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those disclosed herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology disclosed herein is further illustrated by the following examples which in no way should be construed as being further limiting.

Example 1: Portable Transmittance Colorimeter for Rapid Data Acquisition from Enzymatic Paper-Based Microfluidic Devices Disclosed herein is a highly sensitive, portable reader to collect and analyze color changes in microfluidic paper analytical devices in an objective and user-friendly manner. By sandwiching a paper assay between micro-light-emitting diodes and micro-photodetectors, the reader quantifies light transmission through the paper independent of ambient light conditions. To demonstrate the utility of the reader, a single-use paper-based microfluidic assay has been created for measurement of alanine aminotransferase, an indicator of liver health in blood. The paper assay and reader system accurately differentiated alanine aminotransferase levels across the human reference range. Results were provided within 10 minutes and were automatically generated without complex image analysis. Further, this reader was able to differentiate lower concentrations than a desktop scanner, which measures reflected light. Performance of this point-of-care diagnostic rivals the accuracy of lab-based spectrometer tests as well as the timeliness of low-cost portable assays that have historically shown lower accuracy. This combination of features allows flexible deployment of critical diagnostics to resource-poor settings.

Materials and Methods

While microfluidic measurement devices have previously been developed to measure ALT levels in plasma and blood, they contained multiple layers and were optimized for visual interpretation and analysis of results (Pollock et al., Sci Transl Med 2012, 4, 152, 152ra129). To create an ALT assay that is compatible with our transmission-based reader, a device consisting of a single-layer of paper (FIG. 4A) has been developed herein. In the new layout, each device consisted of a single sample port area and four arms, each comprising a channel leading to a circular storage zone and a circular read zone. The storage zones and read zones were both 3 mm in diameter to allow adequate deposition of reagents and adequately encircle the 1.5 mm×1.5 mm LEDs/PDs (FIG. 4B).

To manufacture the devices, the device pattern was created in Adobe Illustrator CS3 and printed the pattern on Whatman No. 1 chromatography paper (GE Healthcare) using a ColorQube 8870 printer (Xerox). Each sheet of assays was passed through an EconRedI oven (Vastex International) at 204° C. to melt the wax into the paper and create the hydrophobic barriers. To allow for reagent addition, the back of the devices was sealed with self-adhesive sheets (Fellowes).

Figures 4A, 4B, 4C:
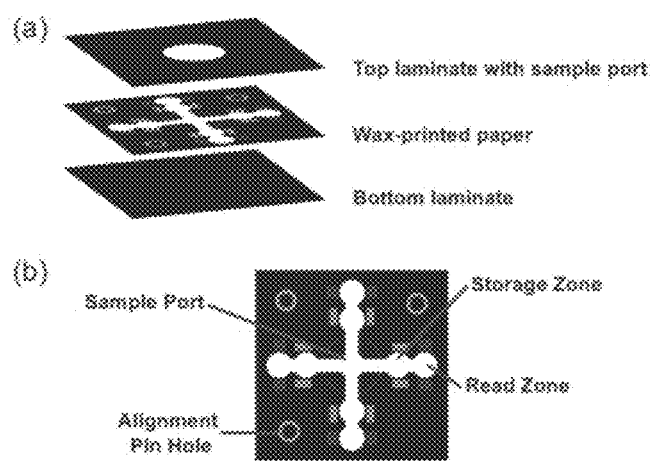
FIGS. 4A-4C are graphs and chemical equations that illustrate paper assay design.

To determine the concentration of ALT in serum, sequence of chemical reactions is used to produce a deep blue color that strongly absorbs red light (FIG. 4C). In these reactions, ALT catalyzes the formation of pyruvate and glutamate from L-alanine and alpha-ketoglutarate. The pyruvate reacts to form hydrogen peroxide in the presence of pyruvate oxidase. Horseradish peroxidase, using hydrogen peroxide, then oxidizes 4-aminoantypyrine and N-ethyl-N-(2-hydroxy-3-sylfopropyl)-3,5-dimethoxyalanine (DAOS) to form a blue dye complex.

Following wax printing and sealing of the paper, color forming reagents were applied to the storage zones and read zones. In the storage zone, 0.50 µL of Reagent 1 consisting of -alanine and alpha-ketoglutarate was spotted. In the read zone, 0.50 µL of Reagent 2 consisting of pyruvate oxidase and horseradish peroxidase was spotted. All devices were dried at room temperature for five minutes. To create a positive control arm, 0.50 µL of Reagent 3 consisting of horseradish peroxidase and hydrogen peroxide was spotted on the read zone of arm 3, and the assays were allowed to dry at room temperature for five additional minutes.

To seal the devices and minimize fluid loss from evaporation, square sections of laminate with 7.5 mm diameter holes were cut using a knife plotter (Craftrobo Silhouette CC330L-20 SD). For each device, laminate was applied directly on top of the center of a dried paper assay with a benchtop laminator. For alignment with the pins in the reader, three 1.5 mm holes were punched in each device at specific, pre-marked locations. Assays were stored at room temperature in a desiccator box until use.

Optoelectronics

Figure 5A:
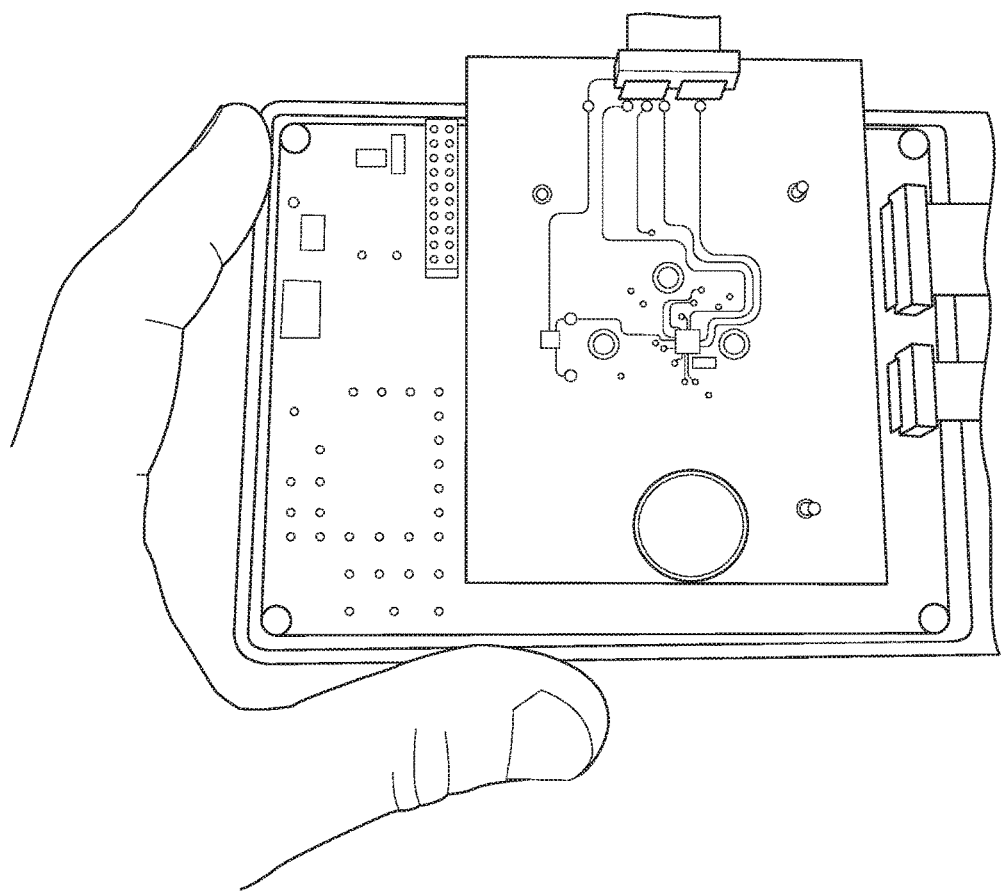
FIGS. 5A-5C are graphs that illustrate the design of a handheld portable reader.
Figure 5B:
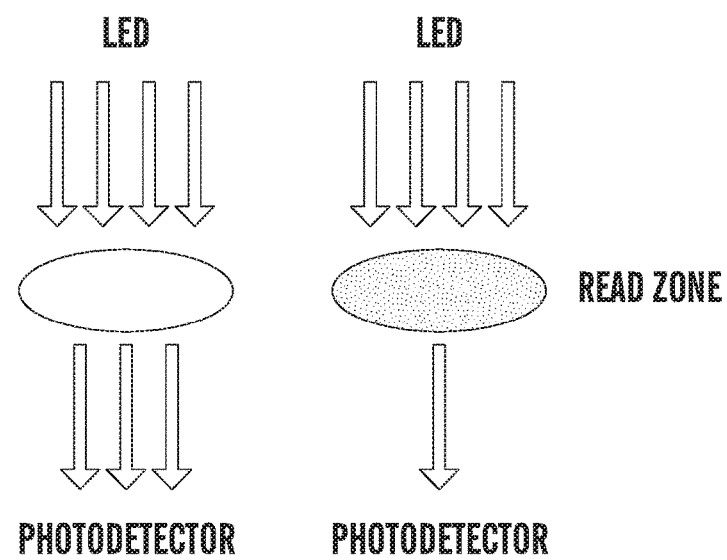
Figure 5C:
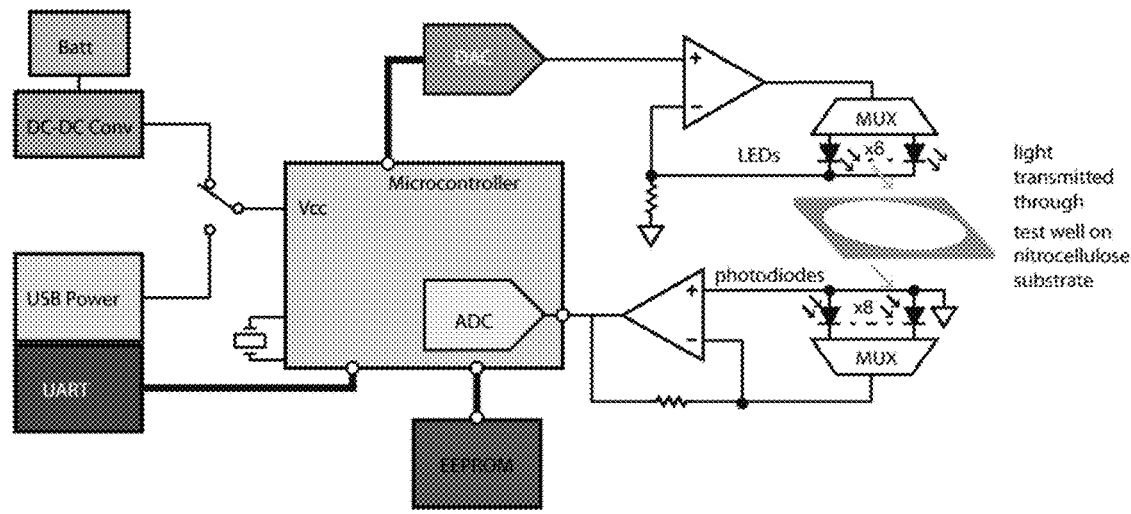

Quantitation of the assay is made possible through integration with the BioStampDx™ optoelectronic platform (FIG. 5A). The paper device is sandwiched between two parts of an electrical circuit designed to interrogate light transmission through the paper. An optoelectronic circuit illuminates the test locations with light-emitting diodes (LEDs) having a center wavelength $\lambda=642$ nm (FIGS. 5B-5C). Light is transmitted through the chromatography paper substrate and detected by a photodiode with peak sensitivity at $\lambda=620$ nm (FIG. 5B). These wavelengths were chosen to maximize the absorption of light by the blue dye complex while minimizing the absorption by possible blood contaminants such as hemoglobin which absorbs light strongly below 600 nm (Zijlstra et al., 1991). Each test and control site is measured by a respective excitation LED and photodiode pair. The intensity of excitation is controlled by a voltage controlled current source, which in turn is adjusted by a 10-bit digital-to-analog converter. A transimpedance amplifier circuit converts the current from the photodiode to a voltage read by the 10-bit analog to digital converter (FIG. 5C).

The diagnostic is operated by a microcontroller (MSP430, Texas Instruments) with firmware written in C using a state-machine design pattern. The state machine is programmed to provide the amplifiers and analog to digital converter enough settling time for accurate and reliable measurements. The state machine steps through the sequence of exciting the LED, sampling the transmitted light and switching to the next measurement channel. Lastly, it handles transferring data to non-volatile memory and/or a computer. Between clocked data samples, the microcontroller is put to sleep to conserve power. The system is powered by a universal serial bus (USB) connection to a desktop or laptop computer and controlled using an accompanying desktop application, or powered from a battery with data stored in non-volatile memory for later retrieval.

Channel to channel variation is reduced by multiplexing the excitation amplifier amongst all LED channels; likewise the photodiode amplifier is multiplexed between measurement channels. This leaves the majority of channel variation to LED and photodiode tolerance. The remaining error is mitigated through software calibration based on control measurements.

Both the voltage controlled current source and transimpedance amplifier exploit feedback topologies that reduce the number of components and cost. Furthermore they were designed to operate on a low supply rail so that this system can be deployed in the field using a laptop USB connection or inexpensive batteries. Tests show that varying the supply voltage by 10% produced less than a 1% variation in measurement results. Respective multiplexers at the voltage controlled current source and at the transimpedance amplifier ensure an independent measurement on each channel. Rail to rail, low power, auto-zeroed amplifiers were selected to reduce errors due to offset and 1/f noise while maintaining low power consumption.

Alignment, Calibration and Error Sources

The microchannels and read zones of the paper assay are aligned using alignment pillars and holes punched through the assay. To reduce the error from alignment issues, 3 mm diameter read zones were designed to readily accommodate the 1.5 $mm^2$ photodetector windows. Thus, the assay can be up to 0.75 mm out of alignment on all sides and results should remain similar. Moreover, intentionally shifting the assay by 0.5 mm produced no significant change in test results.

At each measurement location the photodiode output is measured for a range of LED currents. The relationship between LED current and photodiode output is characterized by a nonlinear equation. The best fit of this equation to the data is computed using a weighted least-squares approach, and the gain of this fit is taken as a measure of light transmission through the assay. For each assay, the gain is first measured when the assay is dry, either preceding or directly following sample application. At this time, the serum has not flowed into the read zone. This calibration corrects for variations in properties of the optoelectronics, assay dimensions and alignment, paper fiber density, dust, etc. All subsequent measurements are normalized to this dry gain. Following the dry calibration, light transmission through each read zone is measured every 15 seconds for 15 minutes. Wetting of the read zone by serum increases the transparency of the assay, increasing the gain. Following this wetting, the amount of blue dye complex formed in each individual read zone reduces optical transmission according to the Beer-Lambert law (Beer, 1852), leading to a reduction in gain over time. The reaction velocity is then calculated as the slope of this reduction.

Results

Figures 6A, 6B:
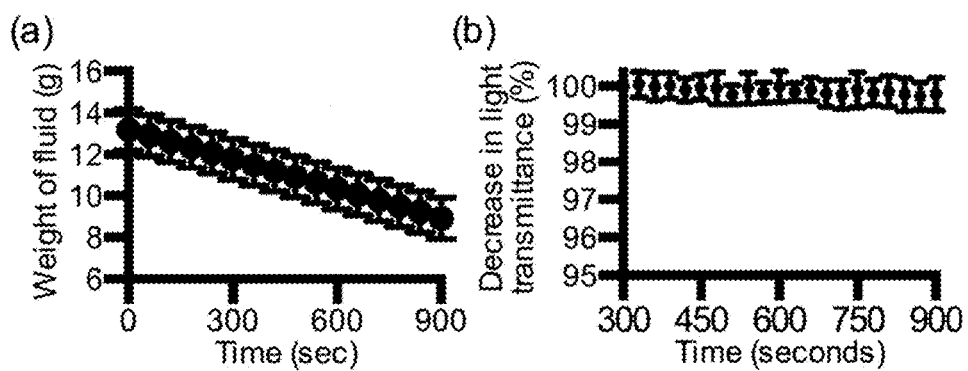
FIGS. 6A-6B are graphs that examines light transmission stability over time.

The effects of evaporation on light transmission were tested in the paper design described herein. To determine how much fluid evaporates from the assay over time, 12.5 mL of serum was added to the sample port of assays and their change in weight was tracked for 15 minutes—the normal duration of the enzymatic assay described herein. In testing conditions of 21° C. and 15% relative humidity, the assays lost an average of 0.3 µL of fluid each minute (FIG. 6A). As this is a significant (36%) decrease in fluid volume over the time period of the assay, it was examined if this evaporation from the open sample port area affected light transmission at the read zones. For each assay, 12.5 µL of serum was added and the change in light transmission at the read zone was measured for 15 minutes. In contrast to the evaporation measurements, the light transmission at the read zone changed less than 1% over the 15 minute period (FIG. 6B). Together, these measurements indicate that sealing the read zone area with laminate prevents evaporation from this specific area and maintains its light transmitting properties.

To demonstrate the function of our portable transmission reader, data were collected from the ALT assay over a wide range of ALT concentrations in human serum. For each concentration, the light transmission was tracked through four read zones in two assays. To run each ALT assay, we placed the assay in the reader and added 12.5 µL of spiked serum. The lid of the tester was closed, an initial calibration was performed on the dry assay to correct for variation in LED strength and alignment, and then light transmission measurements were taken every 15 seconds for 15 minutes.

Figure 7:
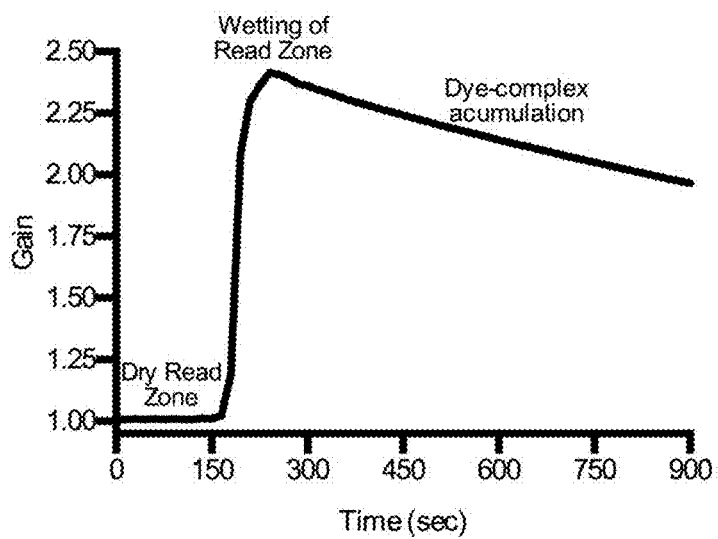
FIG. 7 is a graph demonstrating change in calculated gain over duration of ALT assay. The gain of all channels in the dry state is normalized to 1. As serum flows from the sample port to the read zone, it completely wets the read zone leading to a large increase in light transmission of the paper, which is visualized as a large increase in the gain. If ALT is present, blue dye complex forms at the read zone, increasing over time. The blue dye complex absorbs light, reducing the amount of light transmitted through the paper. This is seen as a reduction in the gain over time.

The measured gain for each channel changed in a predictable manner over the course of the 15 minute read time. Initially, the gain was normalized to 1 for all read zones in the dry state. As capillary forces pulled the serum into the four channels and to the read zones, the read zones became completely wet and their light transmission increased substantially. This is seen as a large increase in the gain as compared to the dry state (FIG. 7). When ALT is present, blue dye complex forms in the read zone and increases in concentration over time. The build up of the blue dye complex absorbs red light, reducing the amount of light transmitted and reducing the gain over time (FIG. 7).

Figures 8A, 8B:
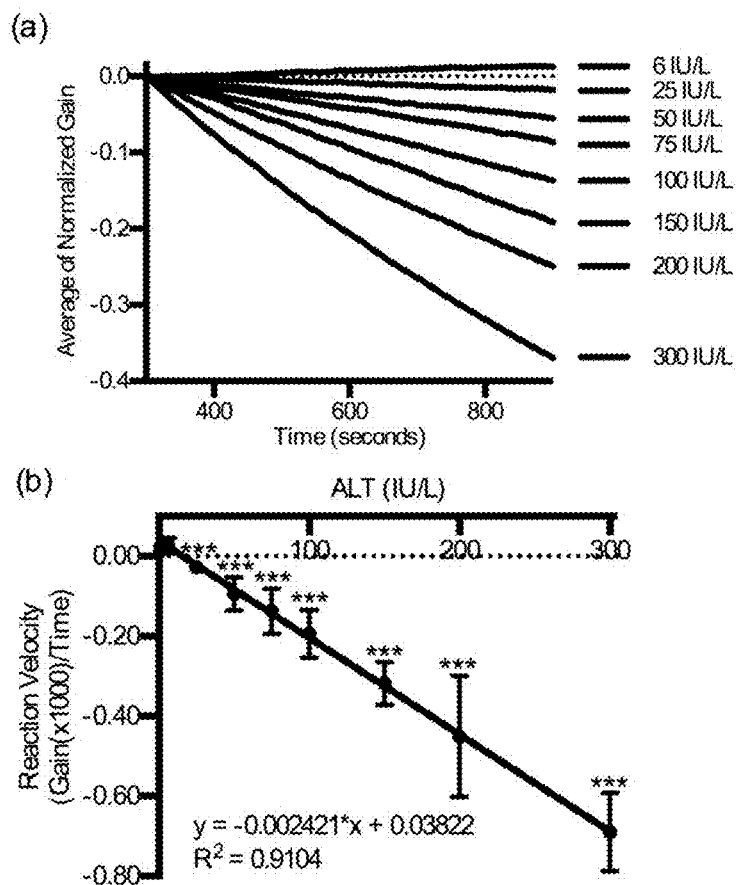
FIGS. 8A-8B are graphs demonstrating the measurement of ALT concentration with a portable transmission reader. Serum with different concentrations of ALT was added to assays and the change in gain at each read zone recorded for every 15 seconds for 15 minutes.

For each ALT concentration, the gain values measured from 300 to 900 seconds were normalized to the 300 second value. Normalization to the 300 second value was chosen because the read zone is fully wetted by 300 seconds, but no significant color has developed. The average of these gain values over time was plotted and demonstrated strong differentiation between the different ALT concentrations (FIG. 8A). The reaction velocity was calculated as the slope of each set of measurements between 300 and 600 seconds and plotted versus the ALT concentration. The reaction velocity changed linearly with ALT concentration (y=−0.002421*x+0.03822, $R^2$=0.9104). To determine if the change in reaction velocity for each ALT concentration was significantly different, we performed a student's t-test to compare each concentration to 6 IU/L. All values above and including 25 IU/L were significantly different than 6 IU/L with p-values less than 0.001 (FIG. 8B).

Figures 9A, 9B:
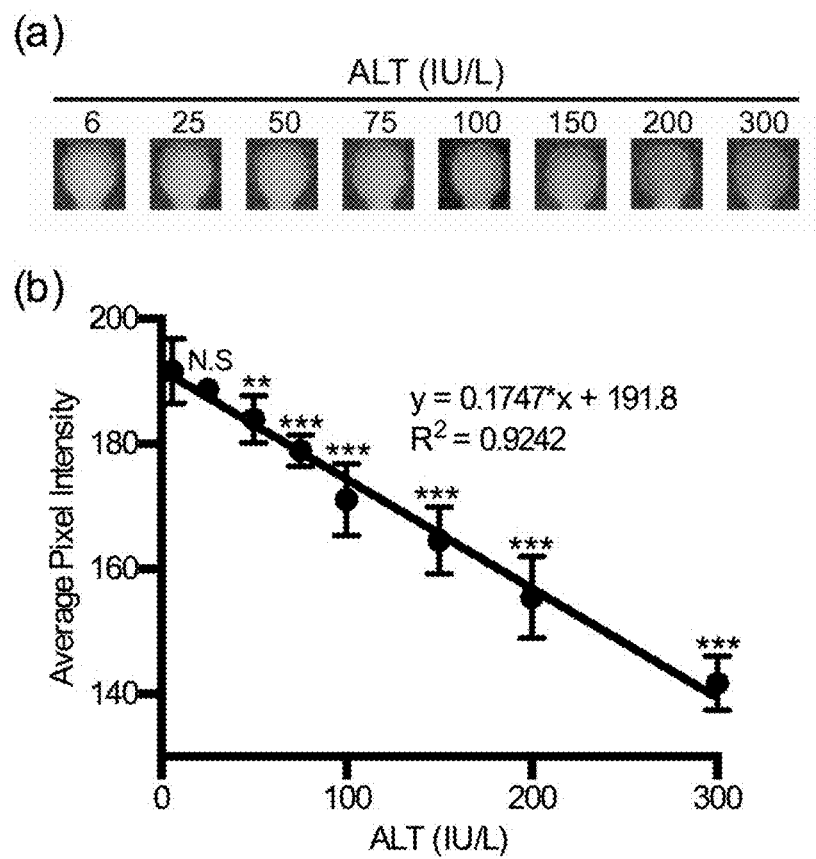
FIGS. 9A-9B are graphs demonstrating the measurement of ALT concentration with scanner. Individual ALT assays were scanned at 16 minutes following analysis in portable transmission reader.

In addition to collecting light transmission data for each ALT assay, each assay was also scanned with a flatbed scanner 16 minutes after serum addition. Representative scans of each ALT concentration demonstrate that it was visually difficult to differentiate low concentrations of ALT (FIG. 9A). To imitate data collected by a reflectance reader, the average pixel intensity in the read zones was quantified using ImageJ software (Schneider et al, Nature Methods 2012, 9, 671-675) and these values were plotted for each ALT concentration. Similar to the light transmission reader, the average pixel intensity changed linearly over the range of ALT concentrations (y=0.1747*x+191.8, $R^2$=0.9242). To determine if the change in average pixel intensity for each ALT concentration was significantly different, a student's t-test was performed to compare the pixel intensity at each concentration to that at 6 IU/L. Although values above 25 IU/L were significantly different from 6 IU/L, the value for 25 IU/L was not (FIG. 9B). Thus the light transmission reader described herein was able to detect smaller changes in ALT concentration than the flatbed scanner.

Discussion

The diagnostic system presented herein enables rapid, point-of-care measurement of ALT concentration from a small sample volume, such as a drop of blood from a finger stick. The paper assay contains channels for plasma distribution and the dried substrates and enzymes. Color formation from different concentrations of ALT builds up over time, allowing quantitation within 10 minutes. The reader contains multiplexed micro-LEDs and PDs to capture the dynamic change in light transmission across each test area. The measured reaction velocity, calculated as the change in light transmission over time, varies monotonically with ALT concentration. The diagnostic can measure ALT concentration in a sample from 6 to 300 IU/L, which is the normal human range. Further, the diagnostic showed better differentiation of low concentrations of ALT than scanning and image analysis.

This diagnostic has several advantages over existing solutions. It only requires a small amount of serum, so blood samples can be taken from a finger stick rather than a venous draw. The paper-based portion of the diagnostic is small, low-cost and disposable, allowing a health care worker to take a large number of assays to remote locations. Unlike previous transmission-based systems, this system is easier to use because pre-wetting with vegetable oil is unnecessary (Ellerbee et al., 2009). Instead, the read zones of the paper assay are sealed with plastic film to minimize evaporation and the paper remains wet throughout the duration of measurement period.

The reader is portable and robust. Unlike many other paper-based point-of-care diagnostics, the approach described herein is highly miniaturized and quantitative, allowing sensitive detection of small concentrations of ALT with high precision. The reader is self-contained with its own processor, allowing it to be used in environments where no power is available. It can be operated by battery or through a USB connection to a laptop or other portable device. It is self-calibrating, eliminating the need for external standards or comparison to central lab facilities. Finally, it can be re-used indefinitely, but is also inexpensive enough to be easily replaced as needed.

Slope based measurements enhance the accuracy of the data for two reasons. First, many data points are collected over the duration of the experiment. The slope is then calculated from all of these data points, making final measurements more resilient to individual read errors and outliers. Second, by measuring the slope instead of the endpoint, slight differences in the thickness of the paper at different points do not significantly affect the measurement.

Alternate approaches for quantifying lateral flow assays include the use of scanners or mobile phone cameras. These approaches measure reflected light, which is dominated by the optical properties of the surface. Consequently, they may not accurately sample the density of absorbers in the assay. Moreover, these approaches require computationally expensive and potentially manual and subjective image processing techniques. In particular, variations in plasma across individuals can significantly affect the results. Accurately measuring the change in optical properties resulting from the addition of plasma requires additional processing. Scanning and imaging methods also use significantly more power than the approach presented here, which limits their utility in resource-poor settings. Finally, mobile phone images in particular are sensitive to ambient light conditions and to uncontrolled adjustment of gain, exposure, and other image parameters by the phone itself, while scanners are often affected by time- and environment-dependent properties of the light source. By automatically measuring a change in absorption under known light conditions, the diagnostic described herein bypasses these issues to provide greater accuracy and precision.

The limitations of our diagnostic include variability in microscale thickness/wetness patterns of the nitrocellulose substrate and differences in light scattering caused by variability in the photodetector and LED output signals. In order to address these problems in less controlled field studies, calibration measurements have been incorporated to account for these perturbations and to normalize out the variability across individual devices. The resulting variability in the hardware and assays has a negligible effect on the measurement.

Although the measurements presented here used a USB connection to a computer for power and data transfer, a 1.5V battery can power the system. Moreover, the microcontroller has sufficient computational power to quantify the results and store them in non-volatile memory for later retrieval by any of a variety of methods. The current system has relatively low throughput, measuring a single assay in ~10 minutes. However, the low cost and small size of the paper assays and optoelectronics make it possible to deploy an array of diagnostics in resource-limited environments.

Demonstrated herein is a diagnostic for point-of-care ALT measurements that is designed for deployment in resource-poor and other point-of-care settings. The accuracy of this diagnostic rivals that of lab-based spectrophotometric tests. Quantitative results are provided in minutes with no need to ship samples off-site. In large-scale production, the readout electronics are expected to cost less than 20 US dollars, while the individual paper assays will cost less than a dollar.

Overall, this diagnostic system is highly flexible and shows great future potential for collection of data from colorimetric assays. In a miniaturized format, dozens of reactions could be placed on a 2 cm² paper assay and produce different colors on the paper. For each of those reactions, a specific LED/PD pair could be chosen to optimize light transmission measurements. The thickness of the paper, concentration of the reagents, and design of the electronics could be tailored to target a specific concentration range. Together, this could allow for a disposable, rapid, low-cost device that evaluates numerous blood analytes simultaneously and can be deployed in far reaches of the world that lack infrastructure.

Example 2: Channel-Specific Calibration for the Devices in Example 1

The signal at the photodetector (PD) can vary across channels on the same diagnostic substrate due to multiple reasons including component variability, positioning variability, and nonuniformity of the nitrocellulose membrane. Provided herein is a procedure for calibrating the system to provide an accurate measurement of absorbance change in the face of this variability.

LED-PD Input/Output Relationship

Figure 10:
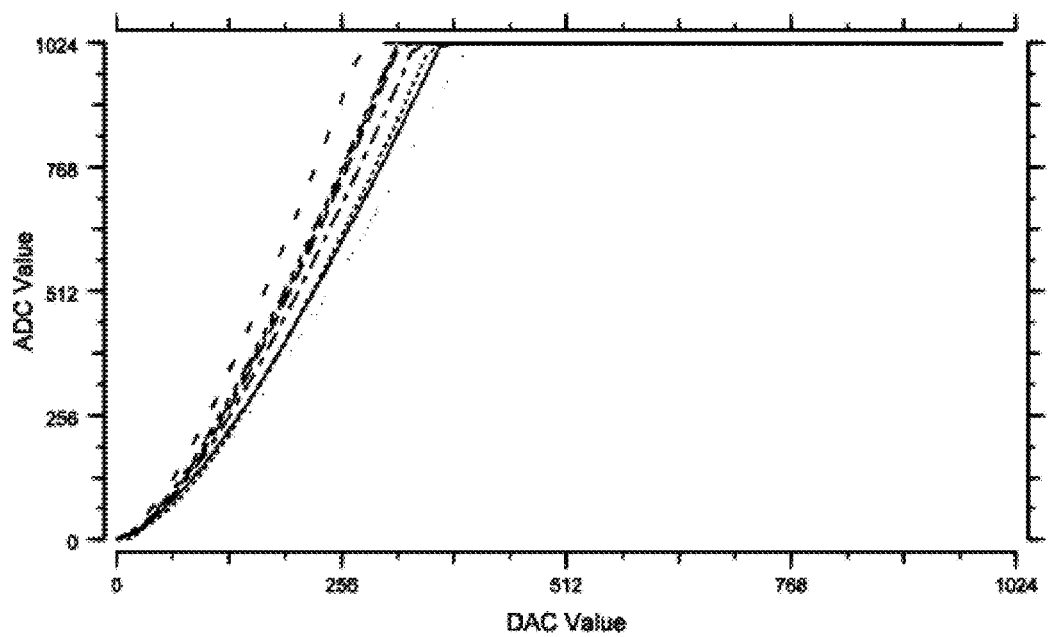
FIG. 10 is a graph that plots the analog-to-digital converter (ADC) output from the PD as a function of the digital-to-analog converter (DAC) input driving the LED for 8 channels of one tester.

FIG. 10 plots the ADC output from the PD as a function of the DAC input driving the LED for 8 channels of one tester. The LED and PD are separated by an air gap, with no nitrocellulose membrane in place. The plot has three regions. Near the origin, there's a minimum DAC value that generates a non-zero ADC output. The width of this region depends on the sample, which suggests that it represents a threshold of the PD; i.e. a certain amount of light needs to hit it before it turns on. Beyond that is a monotonic region where the ADC output grows with DAC value. Finally, there is a saturation region where the ADC output is maximized.

The gain of the system varies across channels. This variation is due to several factors, including component variability and alignment of the motherboard and daughterboard. Consequently the gain must be calibrated separately for each tester. The DAC values are scaled.

Figure 11:
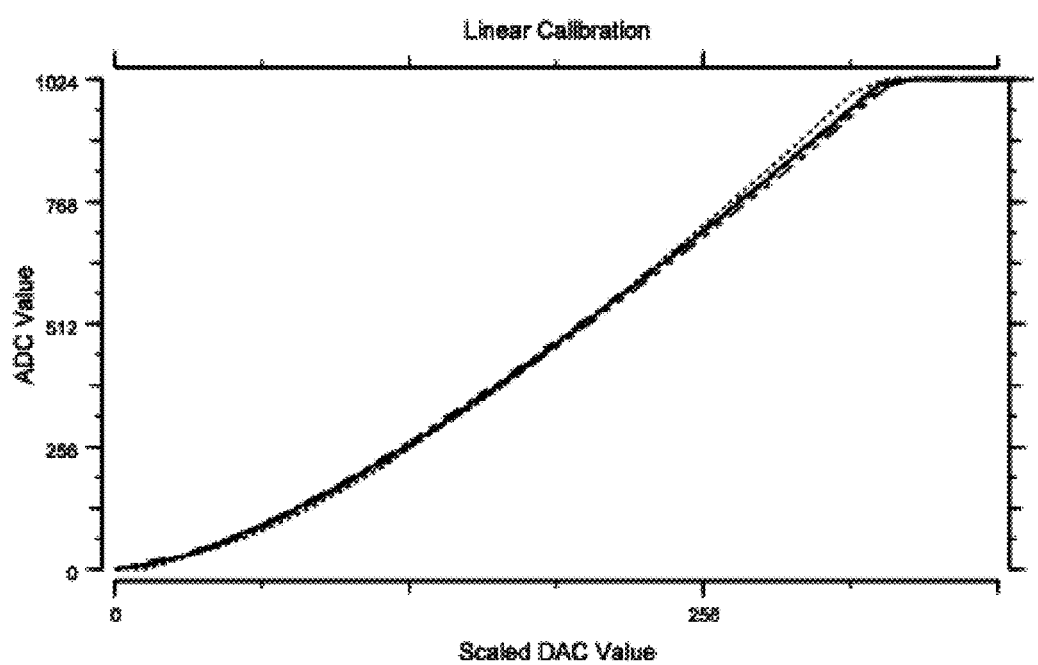
FIG. 11 is a graph showing the results of linearly scaling the DAC values separately for each channel.

FIG. 11 shows the results of linearly scaling the DAC values separately for each channel. The curves overlap, but not exactly. Curves that deviate on the low side for low DAC values also deviate on the high side for higher DAC values. This pattern indicates that the scaling should be nonlinear.

On a log-log scale, the measurements mostly fall on a straight line with a slope of about 1.2. At low DAC values, the curve deviates because of the PD threshold. The equation relating ADC to DAC values is $$V_{ADC} = e^b (V_{DAC} - V_0)^{1.2},$$

where $V_{ADC}$ is the output voltage of the PD, $V_{DAC}$ is the voltage to the voltage-to-current converter driving the LED, $V_0$ is the value at the threshold of the PD, and b is a gain parameter. If the exponent is fixed at 1.2, then one only needs to find $V_0$ and b. Comparing the gain $e^b$ under different conditions (e.g., dry vs wet sample) tells us the relative change in transmittivity.

Because the equation is nonlinear, there's no closed-form solution to the minimum squared error formulation. However, if a value of $V_0$ is chosen, then a closed-form solution for b can be found. That is, the best-fit gain can be found given an input voltage offset.

$$b_{V0} = \frac{\sum_n (1.2 \ln(V_{DAC} - V_0) - \ln V_{ADC}) W(V_{ADC})}{n},$$

where $W(V_{ADC})$ is a weighting term. Since the gain is more tightly constrained by large sample values than small ones, this weight should increase with $V_{ADC}$. Since the input voltages are quantized, $b_{V_0}$ is computed for quantal values of $V_0$ and the one that gives the smallest sum-squared error is chosen.

Figure 12:
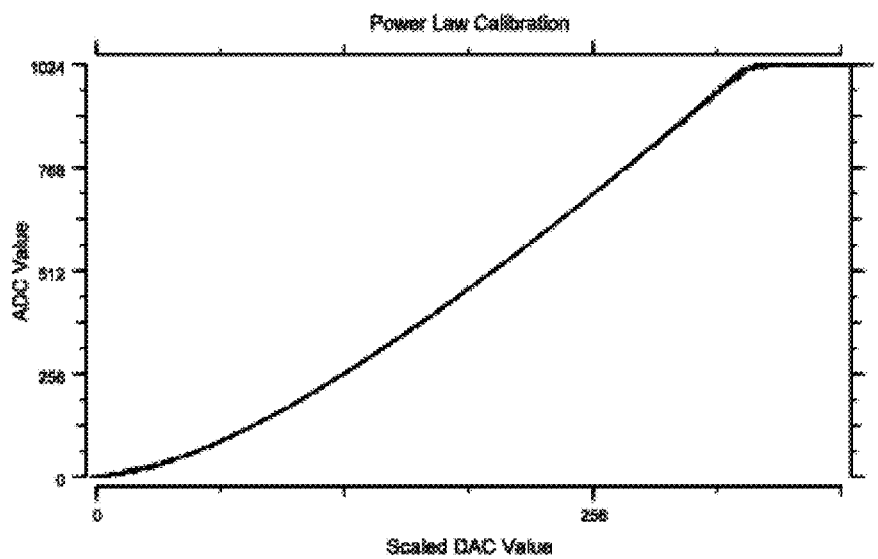
FIG. 12 is a graph showing the corrected curves, which overlap closely over the entire range of values.

The horizontal axis for each curve can be corrected so that the curves have the same gain. The correction equation is given by $$V_{DAC_{new}} = \overline{V}_0 + e^{\frac{b-\overline{b}}{1.2}}(V_{DAC} - V_0),$$

where the horizontal bar denotes averaging. FIG. 12 shows the resulting curves, which overlap closely over the entire range of values.

What is claimed is:

1. A measurement device comprising:
   a diagnostic substrate comprising
   (a) a sample receiver to receive a sample, wherein the sample receiver is at least partially formed in or disposed on the diagnostic substrate;
   (b) a fluidic channel connected to the sample receiver;
   (c) a detection region at least partially formed in or disposed on the diagnostic substrate, wherein the detection region is coupled to the sample receiver by the fluidic channel;
   (d) a control region at least partially formed in or disposed on the diagnostic substrate, wherein the control region is coupled to the detection region by the fluidic channel, and
   a base substrate comprising
   (e) an antenna for near-field communication (NFC) at least partially formed in or disposed on the base substrate;
   (f) electronic circuitry connected to the antenna and at least partially formed in or disposed on the base substrate, wherein the electronic circuitry generates data as a function of an output signal from the sample or a derivative thereof;
   (g) a first portion comprising a first photodetector and a second photodetector connected to the electronic circuitry and at least partially formed in or disposed on the first portion;
   (h) a second portion comprising a first light source and a second light source connected to the electronic circuitry and at least partially formed in or disposed on the second portion, wherein the first portion is folded with respect to the second portion whereby the photodetectors and the light sources are aligned such that light from the first light source passes through the detection region and gets detected by the first photodetector, the light from the second light source passes through the control region and gets detected by the second photodetector, and
   (i) a thin-film battery connected to the electronic circuitry and configured to provide power to the at least one of the first photodetector and the second photodetector, and to provide power to at least one of the first light source and the second light source.

2. The measurement device of claim 1, wherein the diagnostic substrate further comprises a reagent to react with the sample or the derivative of the sample.

3. The measurement device of claim 2, wherein the reagent is a plurality of dyed nanoparticles.

4. The measurement device of claim 1, further comprising a data storage device connected to the electronic circuitry and configured to store the data.

5. The measurement device of claim 1, further comprising a sensor coupled to the sample receiver to detect the presence of the sample.

6. The measurement device of claim 5, wherein the sensor is polled periodically or according to a pre-set schedule to determine the presence of the sample.

7. The measurement device of claim 5, further comprising a timer coupled to the sensor and the photodetector, wherein the timer is activated for a predetermined time when the sample is detected, the predetermined time representing the amount of time to read the sample, the timer activating at least one of the first photodetector and the second photodetector after the predetermined time has been reached, the activated photodetector outputting a measurement value.

8. The measurement device of claim 7, wherein the sensor is deactivated after the predetermined time.

9. The measurement device of claim 1, further comprising a housing for enclosing at least a portion of the measurement device.

10. The measurement device of claim 1, wherein the measurement device is initiated by an external device through a first NFC transaction.

11. The measurement device of claim 10, wherein the measurement device transmits the data to the external device through a second NFC transaction, whereby the external device processes the data to provide quantitative information related to the sample.

12. The measurement device of claim 10 or 11, wherein the external device is a hand-held device or a wearable device.

13. The measurement device of claim 11, wherein the quantitative information comprises at least one of: a glucose level; a T-cell concentration; a microorganism concentration; a water-based pathogen concentration; a bovine serum albumin (BV A) concentration; a bacterial concentration; a viral load; an antigen level; an antibody level; a diagnosis of tuberculosis; a diagnosis of dengue fever; a cardiac enzyme concentration; and a diagnosis of malaria.

14. The measurement device of claim 1, wherein the first portion is folded over the second portion such that the first portion and the second portion sandwich the diagnostic substrate.

15. The measurement device of claim 1, wherein the second portion is folded over the first portion such that the first portion and the second portion sandwich the diagnostic substrate.

16. The measurement device of claim 1, wherein the sample is a fluid sample.

17. The measurement device of claim 16, wherein the fluid sample is selected from the group consisting of blood, serum, saliva, and urine.

18. The measurement device of claim 1, wherein the diagnostic substrate comprises a paper-based portion.

* * * * *